(12) United States Patent
Tedesco

(10) Patent No.: US 9,149,342 B2
(45) Date of Patent: Oct. 6, 2015

(54) SYSTEM AND METHOD FOR A BONE ENGAGING DENTAL IMPLANT SURGICAL STENT PLACEMENT SYSTEM

(71) Applicant: James Lee Tedesco, Orchard Park, NY (US)

(72) Inventor: James Lee Tedesco, Orchard Park, NY (US)

(*) Notice: Subject to any disclaimer, the term of this patent is extended or adjusted under 35 U.S.C. 154(b) by 70 days.

(21) Appl. No.: 13/874,901

(22) Filed: May 1, 2013

(65) Prior Publication Data

US 2014/0329196 A1    Nov. 6, 2014

Related U.S. Application Data

(60) Provisional application No. 61/691,230, filed on Aug. 20, 2012.

(51) Int. Cl.
*A61C 1/08* (2006.01)
(52) U.S. Cl.
CPC ..................... *A61C 1/084* (2013.01)
(58) Field of Classification Search
CPC .............................. A61C 8/0001; A61C 1/084
USPC ....................................................... 433/75, 76
See application file for complete search history.

(56) References Cited

U.S. PATENT DOCUMENTS

| 5,967,777 | A | 10/1999 | Klein et al. | |
|---|---|---|---|---|
| 5,989,025 | A * | 11/1999 | Conley | 433/76 |
| 6,869,283 | B2 | 3/2005 | Sussman | |
| 7,086,860 | B2 * | 8/2006 | Schuman et al. | 433/75 |
| 2005/0245940 | A1 * | 11/2005 | Brock | 606/99 |
| 2006/0263743 | A1 * | 11/2006 | Tedesco | 433/76 |
| 2009/0239197 | A1 * | 9/2009 | Brajnovic | 433/174 |
| 2009/0291414 | A1 * | 11/2009 | Wang | 433/174 |
| 2012/0009544 | A1 * | 1/2012 | Lin | 433/172 |
| 2014/0026419 | A1 * | 1/2014 | Haber | 29/896.1 |

* cited by examiner

*Primary Examiner* — Ralph Lewis
(74) *Attorney, Agent, or Firm* — Vincent G. LoTempio; Kloss, Stenger & LoTempio; David Stephenson

(57) ABSTRACT

A bone engaging dental implant surgical stent placement system comprising: a gingival depth impression pin, wherein the gingival depth impression pin is placed in a patient's bony ridge to establish a penetration site. An impression is then created of the patient's bony ridge by placing an impression material around the gingival depth impression pin and the patient's gingival tissue. A stent fabrication guide tube is then placed over the gingival depth impression pin, and a dental stone is poured into the impression to create a working model, with a penetration hole for placing a stent fabrication guide pin into the penetration hole. A baseplate matrix is then molded around the stent fabrication guide pin to create the stent, which positions a pilot drill guide tube to actively engage with the bony ridge and to act as a drill guide when making a pilot hole.

16 Claims, 10 Drawing Sheets

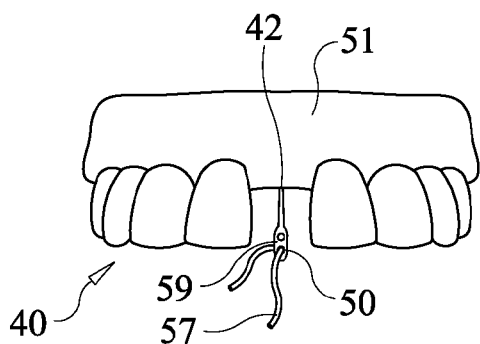 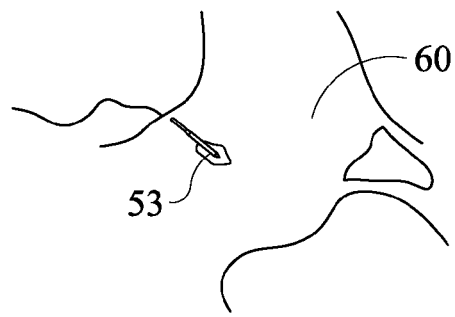
FIG. 3A  FIG. 3B
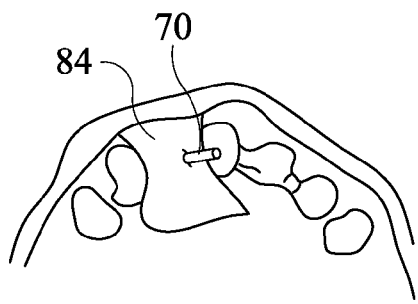 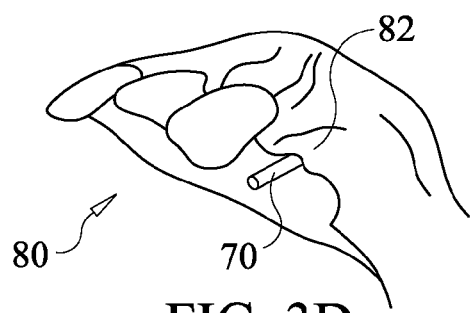
FIG. 3C  FIG. 3D
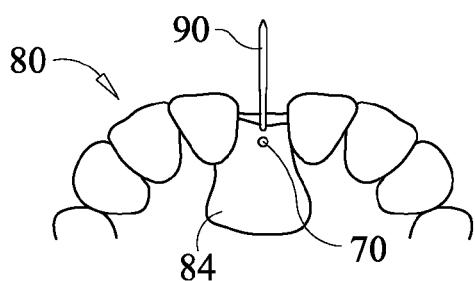 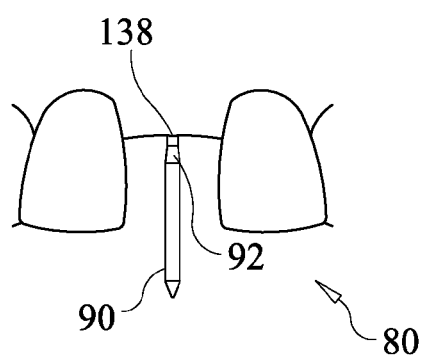
FIG. 3E  FIG. 3F
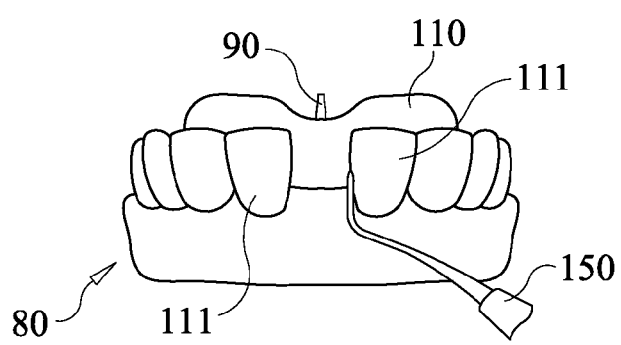 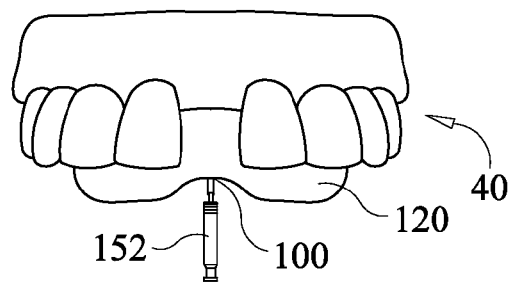
FIG. 3G  FIG. 3H

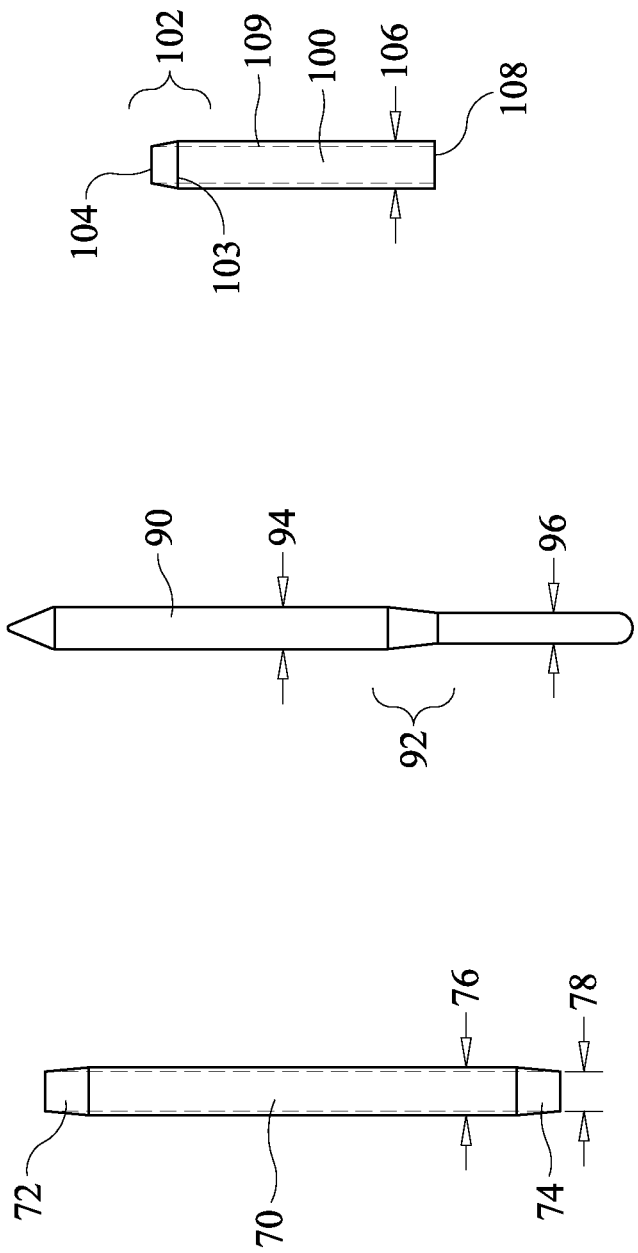

SYSTEM AND METHOD FOR A BONE
ENGAGING DENTAL IMPLANT SURGICAL
STENT PLACEMENT SYSTEM

CROSS REFERENCE TO RELATED
APPLICATION

This application claims the benefit of U.S. Provisional Application of James L. Tedesco, Ser. No. 61/691,230, filed 20 Aug. 2012, having the title BONE ENGAGING DENTAL IMPLANT SURGICAL STENT PLACEMENT SYSTEM, which is incorporated herein by reference in its entirety.

FIELD OF THE DISCLOSURE

The present invention relates to a dental implant surgical stent placement system and method, more particularly, to a bone engaging dental implant surgical stent placement system, including case work-up protocols, associated instrumentation and methods of manufacturing, laboratory fabrication procedure protocols, surgical protocols and doctor training protocols.

BACKGROUND

It is known in the art to use dental implants to replace missing teeth in a patient's mouth using various procedures. Dental implant procedures generally involve drilling a pilot hole into the jawbone of a patient and inserting an implant body into the hole provided. The crown is then cemented to the top section of the implant abutment to complete the procedure. There are various prior art stents used as drill guides for drilling the initial pilot hole. These prior art procedures commonly require the purchase of high-tech, very expensive apparatuses. The pilot hole in an implant procedure is critical since it provides the hole into which the implant will be based and must be drilled along an acceptable path to insure maximum strength to the eventual implant. Many implant stents in use today are fabricated with thick vacuum formed plastic that covers the biting surfaces of many teeth adjacent to the surgical site. These stents, by virtue of their size and thickness above the teeth, drastically reduce access to the surgical site, especially in the posterior molar regions where the tongue and cheek muscles already reside making multiple instrumentation procedures exceedingly difficult, if possible at all.

In addition to the large stent, a directional device with a three-inch long handle is required to help direct the pilot drill. Not only does it restrict vision even further, the long "lever" easily torques the stent right or left and is difficult to hold steady when the surgeon has to hold the drill at the proper angle with one hand, hold the directional device's handle with the other, keep the stent down without twisting it left or right, all the while fighting the tongue and cheek muscles from throwing the pilot drill off line. A water syringe and suction tip are thrown into the mix, reducing vision further. It is almost impossible in these prior art procedures to see if the pilot hole and drill are accidentally sliding down outside the surface of the bone because the dentist cannot determine whether they are entering at the right spot or at the right angle. To illustrate, most of the implant placement failures and near failures involve a bony ridge on the posterior ridge. Starting a pilot hole, with a drill guide, which is 3, 4, 5, or 6 mm away from the dense bone of a bony ridge is a very difficult proposition. A high speed round bur does not always help. If the round bur, that starts the pilot hole is off line by even 0.5 mm, the implant abutment will be angled so far out of position that a premade crown may not fit properly even with a long adjustment process.

In addition, getting multiple one-piece implants (4 to 10) into their proper positions and at a 90 degree angle to the biting surface of the adjacent teeth often becomes a struggle for the surgeon and patient alike. Also, it is even more difficult to place multiple implants (4 to 10) in an extremely precise parallel arrangement when placing one-piece implants around the curves of the jaw, while remaining cognizant of the need to keep the body of the one-piece implant in the approximate middle of the jawbone's depth buccal lingually.

The severity of these problems are magnified as narrow diameter bone drills less than 1.5 mm in diameter are flexible and seldom maintain the angle desired by the operator when drilling freehand into the jawbone because the jawbone is a mixture of soft and hard tissues and air pockets. Narrow diameter bone drills also will flex away from hard tissue into the areas of least resistance, i.e., soft tissue and air pockets, rendering it very difficult to drill free-hand pilot holes at the angles intended and necessary for efficient and immediate attachment of pre-fabricated prosthetic devices, i.e., dental crowns, bridges, implant retained partials over dentures, hybrid dentures and traditional full over dentures.

Another issue is the larger diameter pilot drill bit that one-piece implant companies sell in their implant kits. These larger diameter pilot drill bits when drilling into less than dense bone often remove the very bone that would be necessary for initial implant stabilization requirements. When this happens, drops of blood bubble from the hole on a drop-by-drop basis, thereby causing the procedure to be aborted, which is expensive and bad for patient confidence.

Also, current surgical stent guide systems do not provide adequate guidance for narrow diameter pilot drill bits during a majority of its travel into and through the bony ridge because the pilot drill guide tubes, end 1 to 4 millimeters above the surface of the bone. Additionally, many of the current surgical stent guide systems are also, large with bulky associated instrumentations precluding the effectiveness in the posterior regions of the mouth where most patients require implants. Furthermore, the current surgical stent guide systems also do not work well because the tolerances used for the drill guides are so lax and the associated instrumentations are so bulky, that it is easy for the dentist to drill pilot holes outside the surface of the bone instead of drilling into the bone at the previously determined angle and depth.

Many dentists attempting to use these current surgical stent drill guide systems for one piece implants find major problems arise and become discouraged when cases fail to integrate, or are so far outside ideal position that it is impossible to place prosthetics in a good cosmetic and/or functional position. Also many other surgical stent drill guide systems are sent to a dental laboratory, where the cases are treatment planned and the initial pilot-hole penetrations are dialed into the stent by a non-dentist lab technician. Trusting a $4,000 implant case to a technician seems foolhardy at best, and may result in a failed surgery. If the stent is inaccurate, the dentist will not be able to remake the stent quickly, as it would require the dentist to send for a new stent, often taking weeks for delivery, thus the dentist will have to abort the surgery and incur additional expenses.

Another issue with the current surgical stent drill guide systems is the type of baseplate matrix material used. Numerous materials are used to make dental baseplate's, retainers, bite blocks and bruxism (grinding) stents. Most implant guide stents are made of vacuum formed clear resin sheets. These types of stents do not allow the dentist to make implant guide stents the same day as surgery. Typically, the patient must come in for a consultation where the dentist takes an impression and the patient then must leave and return on a later day for surgery when the dentist has made the implant guide stent. Also, many stents are expensive as they use such equipment as CT Scans, or three-dimensional (3D) stereo lithography techniques.

Some current surgical stent drill guide systems tried to address some of the above issues as they provided a surgical stent drill guide system, which contacted the bone at its inferior surface providing some resistance to movement as the pilot hole was created. However, these surgical stent drill guide systems did not allow for active engagement with the bony ridge as the pilot drill entered the surface of the bony ridge. Thus, these surgical stent drill guide systems did not allow for precise directional control. Also, these surgical stent drill guide systems did not allow for immediate fabrication in a few minutes and they did not allow for the stent to be made or "remade" during surgery when necessary.

Other prior art surgical stent drill guide systems require expensive computer imaging, 3D CT scans, and/or computer assisted digital x-ray images, for stent fabrication. These time consuming and expensive surgical stent drill guide systems such are the sorts of items that have kept implant dentistry out of financial reach of the average patient. These prior surgical stent drill guide systems do not (nor is it their intention) provide the accuracy necessary to cement a premade crown the same day as implant surgery.

Thus, a heretofore unaddressed need exists in the industry to address the aforementioned deficiencies and inadequacies.

SUMMARY

The present disclosure provides a system and method for a novel low cost implant stent or drill guide used to accurately guide a drill bit needed for the critical initial pilot hole. Prior dental stents and implant procedures required the purchase of high-tech, very expensive apparatuses, which are bulky and do not allow for active engagement with the patient's bone or allow for precise directional control. Thus, an unaddressed need exists in the industry to address the aforementioned deficiencies and inadequacies.

Briefly described, in one embodiment is a bone engaging dental surgical stent comprising a gingival depth impression pin, which has a penetration end and an impression retention end. The penetration end is placed in a patient's bony ridge at a location on a patient's gingival tissue to establish a penetration site. An impression is created of the patient's bony ridge by placing an impression material around the gingival depth impression pin and around the patient's gingival tissue. A stent fabrication guide tube is then placed over the gingival depth impression pin, wherein a dental stone is poured into the impression surrounding the stent fabrication guide tube to create a working model with a penetration hole for placing a stent fabrication guide pin into the penetration hole. A baseplate matrix is molded around the stent fabrication guide pin in the working model to create the bone engaging dental implant surgical stent, which positions a pilot drill guide tube to actively engage with the bony ridge at the penetration site and to act as the drill guide when making the pilot hole.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A shows a patient's mouth with a gingival depth impression pin placed at a preferred central penetration site determined by the dentist.

FIG. 3B shows an impression taken of the patient's mouth with a gingival depth impression pin recording the penetration.

FIG. 3C shows artificial gingival tissue molded around a gingival depth impression pin.

FIG. 3D shows the stent fabrication guide tube penetrating out from the working model.

FIG. 3E shows the working model with artificial gingival tissue and a stent fabrication guide pin being placed in the stent fabrication guide tube.

FIG. 3F shows a bevel of the stent fabrication guide pin as it emanates from the stent fabrication guide tube in the working model.

FIG. 3G shows baseplate matrix being molded around a stent fabrication guide pin, as well as the adjacent teeth.

FIG. 3H shows a finished stent with a pilot drill guide tube placed in the stent and a pilot bone drill bit placed within the pilot drill guide tube.

FIG. 7A shows a stent fabrication guide tube.

FIG. 7B shows a stent fabrication guide pin.

FIG. 7C shows a pilot drill guide tube.

DETAILED DESCRIPTION OF THE EMBODIMENTS

Figure 1:
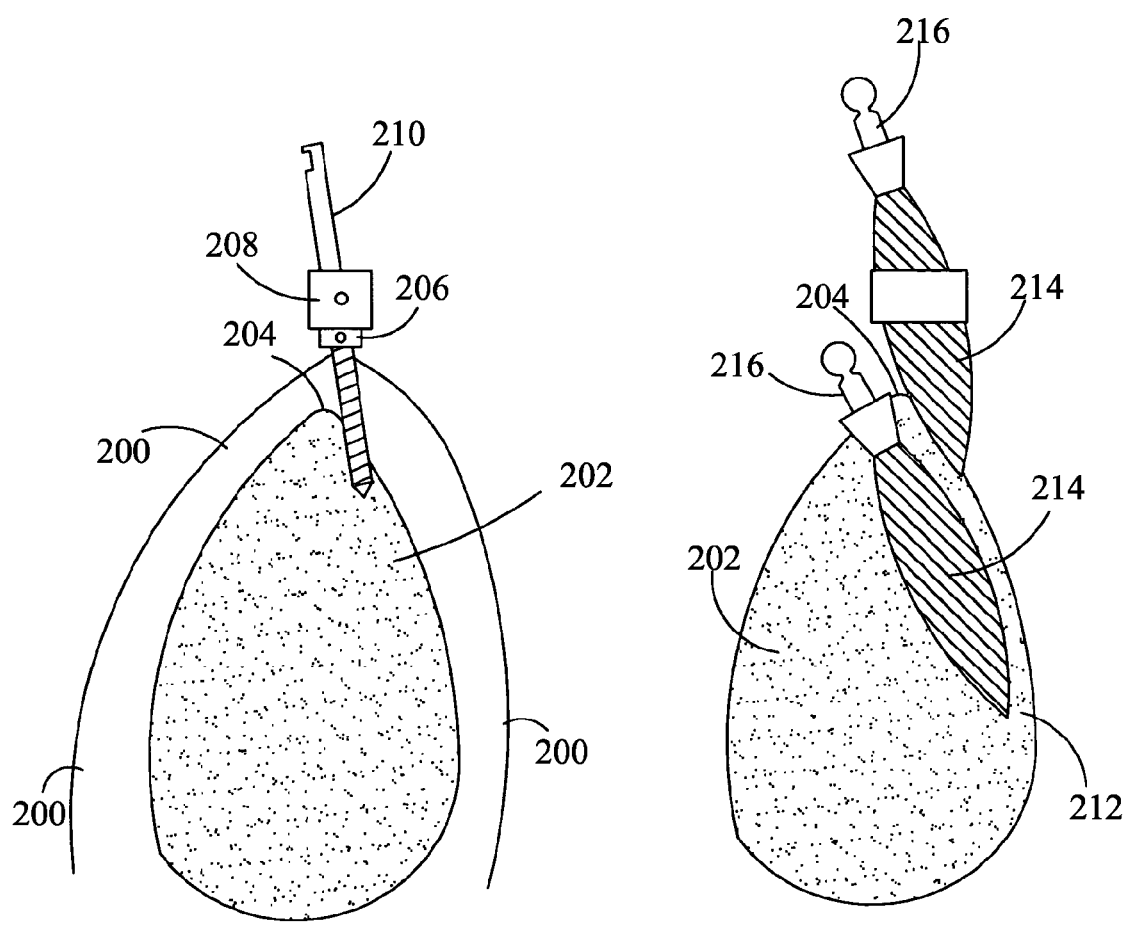
FIG. 1 is a perspective view of the prior art stent and an illustration of potential problems.

Reference is now made in detail to the description of the embodiments as illustrated in the drawings. While several embodiments are described in the connection with these drawings, there is no intent to limit the disclosure to the embodiment or embodiments disclosed herein. On the contrary, the intent is to cover all alternatives, modifications, and equivalents.

It should be clearly understood that like reference numerals are intended to identify the same structural elements, portions, or surfaces consistently through out the several drawing figures, as may be further described or explained by the entire written specification of which this detailed description is an integral part. The drawings are intended to be read together with the specification and are to be construed as a portion of the entire "written description" of this invention as required by 35 U.S.C. §112.

Currently it is known in the art that dental implant surgical stent placement systems suffer from the following issues: first, it is difficult to get a pilot hole started in a patient's bony ridge and at a proper angle, without sliding down an outside surface of the bony ridge when dealing with thin resorbed bony ridges and flapless surgical protocol. Second, it is an extremely difficult procedure when using the current dental implant surgical stent placement systems to place multiple implants (4 to 10) in an extremely precise parallel arrangement when placing one-piece implants around the curves of the bony ridge, while remaining cognizant of the need to keep the body of the one-piece implant in the approximate middle of the patient's jawbone depth buccal-lingually. Third, many of the current dental implant surgical stent placement systems use a pilot drill bit having a diameter, which is too large to accommodate a patient's thin bony ridge. These larger drill bits often remove the very bone that would be necessary for initial implant stabilization requirements in less than dense bone. Lastly, the large size of the current dental implant surgical stent placement systems instrumentation make use in the second ($2^{nd}$) molar region and maxillary tuberosity almost impossible. Thus, there is a need for a bone engaging dental implant surgical stent placement system wherein the above deficiencies and other deficiencies have been obviated in a novel manner by the present claimed disclosure, as will be more apparent upon studying the remaining disclosure.

It should be noted that during the method of using the bone engaging dental implant surgical stent placement system, the dentist becomes intimately involved with the soft gingival tissue's thickness, density, shape, and irregularities of the bony ridge at the implant site. The dentist thus gains a comprehensive understanding of the patient's implant site, with this understanding the dentist is able to provide for the patient a quick, efficient, yet extremely precise, usually painless implant and prosthetic procedure. The stents of the claimed invention are custom fabricated by a dental surgeon for each implant site before or during a surgical implant placement. Because, the claimed disclosure provides exceptional precision placement of one-piece dental implants the dentist may place a crown on the implant the same day as an implant body is inserted. In addition the dental surgeon quickly and efficiently is able to place a pre-made denture on multiple implant bodies the same day as surgery. The bone engaging dental implant surgical system provides the dentist of average ability to provide high precision pilot drill holes with less chance of failure or mishap, which patients will appreciate with the finished results especially in extremely challenging cases as will become apparent as the description proceeds.

An example of an embodiment of the claimed disclosure, is a system and method for a bone engaging dental implant surgical stent placement system comprising, a uniquely precise surgical stent, used to drill pilot holes, that is particularly useful when treating patients with severely resorbed, and/or knife edge bony ridges as it actively engages the bone at its inferior surface and fixes itself to teeth and the gingival ridge at its superior surface. The claimed disclosure provides an extremely stable stent with pilot drill guide tubes that provide maximum guide plane surfaces for a pilot drill bit to progress through the bony ridge. The pilot drill guide tube is anchored inside the bone ridge and a surgeon utilizing "Proceed and Verify" protocol may verify the pilot drill guide tubes proper positioning. The "Proceed and Verify" protocol comprises of taking x-rays and by probing with a dental explorer, which will insure later the success of a pilot hole creation. Further, the instant disclosure includes a method for fabricating a stent utilizing custom designed laboratory instrumentation and procedural protocols that aid in providing the necessary precision and parallelism of a one-piece narrow diameter implant that is required for a multiple implant placement in overlay denture cases and the staggered arrangement required in fixed-bridge cases. Though the bone engaging dental implant surgical stent placement system of the claimed disclosure may be adapted for many different size pilot drill bits, (both length and outside diameter) the breadth and scope of the system itself remains the same.

Figure 2:
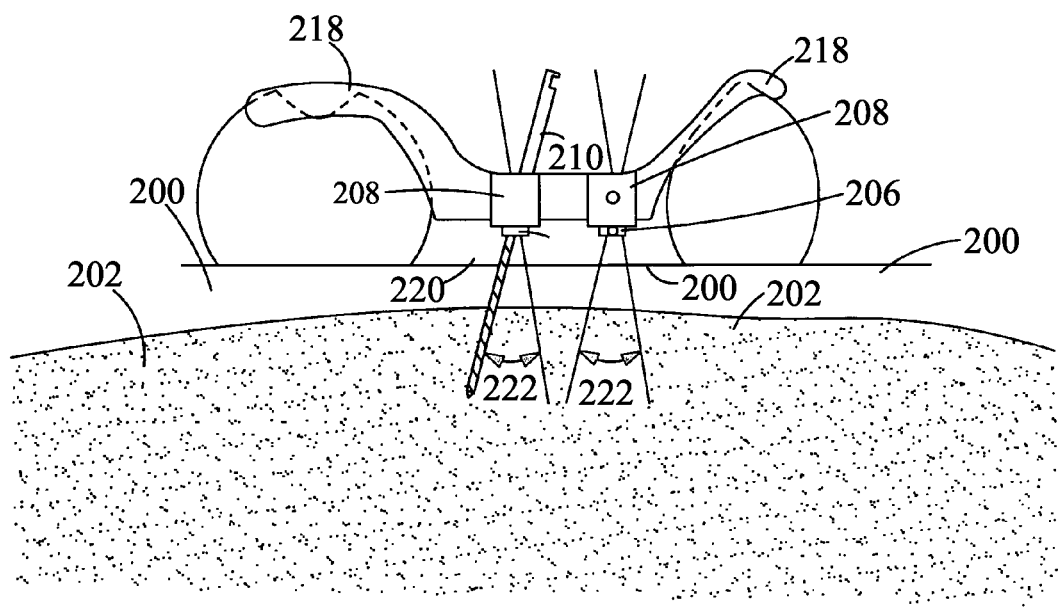
FIG. 2 is another perspective view of the prior art stent and an illustration of how problems can occur.

Adverting now to the drawings, with reference to FIGS. 1 and 2, the prior art stent is illustrated. In prior art stents 218 and accompanying procedures, a bone drill 210 has too much play, due to the large distance between a drill guide 208 and a bone 202. A guide 208 and a directional device 206 stops atop a patient's tissue 200 and must travel generally from 2 to 6 mm distance 220 before it contacts bone 202. If pilot drill 210 cannot engage a bone's knife edge 204, it will slide down a buccal plate 212 of bone 202, chewing up attached gingiva. The result is an implant body 214 or an abutment 216 out of position and at an angle to the long axis of the ridge. Implant body 214 may also be dangerously close to buccal plate 212.

In FIG. 2, a side view of prior art stent 218 having a placement ring 208 and a directional device 206 is shown where directional device 206 stops above patient's gum tissue 200. Bone drill 210 may have too much play and usually moves a somewhat large distance shown at 222, therefore the excessive play in prior art drill guides 208 and drill guide directional devices 206 allow for easy misplacement of the pilot hole. An object of the present invention, as earlier noted, is to provide a novel stent devoid of these prior art disadvantages.

FIGS. 3A-3H shows the fabrication of a stent.

FIG. 3A shows a patient's mouth 40 with a gingival depth impression pin 50 placed at a preferred central penetration site 42 determined by the dentist. Preferred penetration site 42 is patient specific based on such factors as the width of a patient's bony ridge. Gingival depth impression pin 50 is pushed through gingival tissue 51 until it comes into contact with the bony ridge. Thereafter, an impression is taken of patient's mouth 40 with gingival depth impression pin 50 in patient's mouth 40. Gingival depth impression pin 50 as shown in FIG. 7E has a penetration end 53 and an impression retention end 55. The penetration end is in the shape of a pin or a cuneated or wedge-shaped point, capable of penetrating gingival tissue 51. Also, the penetration end may have horizontal cuts or ridges designed to create retention in gingival tissue 51, resulting in "tug back" during the removal of the impression from patient's mouth 40. The penetration end has the same diameter as a pilot drill bit. The impression retention end is of a geometry that allows for the attachment of a recovery cord 57, as well as a piece of dental floss, or other retentive elements, which allow for an impression material to grab during the removal of the impression. The geometry of the impression retention end is of a shape, having a flat rectangular end with small holes 59 within the flat rectangular shape. Holes 59 are for the purpose of receiving recovery cord 57. Recovery cord 57 is comprised of simple string, thread, dental floss or any other like material so as to allow the dentist the ability to retrieve a dislodged, gingival depth impression pin 50 during the procedure, thus preventing gingival depth impression pin 50 from falling to the back of the patient's mouth. In alternative embodiments in accordance with the disclosure, the impression retention end may be any shape, for example square, triangular or a generally hook shape end for connection to recovery cord 57. Recovery cord 57 is placed through holes 59, allowing the dentist to pull gingival depth impression pin 50 out of the impression, once the dentist is done using the impression to mold a working model as shown in FIG. 3D.

FIG. 3B shows (the inside of) an impression taken of the patient's mouth with the gingival depth impression pin recording the penetration. When impression 60 is removed as shown, the inside of impression 60 reveals penetration end 53 of the gingival depth impression pin. Exposed penetration end 53 of the gingival depth impression pin represents the depth of the patient's gingival tissue at the penetration site in the patient's mouth.

FIG. 3C shows artificial gingival tissue 84 molded around the gingival depth impression pin and a stent fabrication guide tube 70. The gingival depth impression pin with artificial gingival tissue 84 will be used as an anchor for stent fabrication guide tube 70. The preferred thickness of artificial gingival tissue 84 is determined by following a method of determining tissue thickness or a "Bone Sounding" protocol known by dentists, wherein, the dentist determines the shape of the patient's bony ridge. After artificial gingival tissue 84 has been molded to the preferred thickness stent fabrication guide tube 70 is placed over the gingival depth impression pin. Dental stone is then poured into the impression and hardened, to create working model 80 as shown in FIG. 3D.

FIG. 3D shows stent fabrication guide tube 70 penetrating out from working model 80. The penetration site is located at a central location on bony ridge 82. The artificial gingival tissue may be removed (as shown) after working model 80 is poured and hardened, which will reveal a three-dimensional (3D) representation of bony ridge 82 under the artificial gingival tissue. A penetration hole (not shown) may be adjusted or moved by experimenting with working model 80, by using and following the lost gingival technique.

Generally the lost gingival technique is used for identifying the shape of bony ridge 82 before dental implant surgery. The lost gingival technique allows for fabrication of an accurate stent 120 (as shown in FIG. 3H) without the added expense and time restraints of a laboratory or CT scan computer generated surgical guide. By utilizing traditional bone sounding procedures and/or gingival depth impression pins, the dentist can design working model 80 that upon removal of the artificial gingival tissue will reveal a three dimensional (3D) representation of bony ridge 82. This allows the dentist to see the top of bony ridge 82 and identify the preferred placement of the penetration hole. Revealing bony ridge 82 in this manner allows for accurate fabrication of stent 120 (as shown in FIG. 3H) or allows the dentist to check the accuracy of a previously made bone engaging dental implant surgical stent.

FIG. 3E shows working model 80 with artificial gingival tissue 84 and a stent fabrication guide pin 90 being placed in stent fabrication guide tube 70. Stent fabrication guide tube 70 remains in working model 80 and artificial gingival tissue 84 is placed back on working model 80. A stent fabrication guide pin 90 is then placed in stent fabrication guide tube 70 providing a secure metal on metal interface allowing the dentist to bend stent fabrication guide pin 90 slightly without breaking working model 80.

FIG. 3F shows a bevel of the stent fabrication guide pin as it emanates from the stent fabrication guide tube in the working model. Working model 80 having stent fabrication guide pin 90 placed at penetration hole 138 is in condition to receive a soft baseplate matrix molded around stent fabrication guide pin 90. Stent fabrication guide pin 90 has a length, shape and outside diameter designed to create an opening in the baseplate matrix to work in unison with round surgical length dental drill bits, as well as the stent fabrication guide tube and a pilot drill guide tube. Stent fabrication guide pin 90 has a larger 94 and a smaller 96 outside diameter (as shown in FIG. 7A). The larger outside diameter 94 creates a hole in the baseplate matrix that mirrors the length of the dental drill bit, while the smaller outside diameter 96 is of an approximate diameter to firmly enter and engage penetration hole 138 of working model 80. In the middle of stent fabrication guide pin 90 is a bevel 92, which creates an area of constricted resin in the baseplate matrix, for the purpose of keeping the pilot drill guide tube tight in the baseplate matrix during surgery.

FIG. 3G shows baseplate matrix 110 being molded around stent fabrication guide pin 90, as well as adjacent teeth 111 in working model 80. A dental tool 150, such as a Hollenbeck, may be used as well as the dentist's fingers to apply pressure to baseplate matrix 110, pinching baseplate matrix 110 in-between teeth 111 and into stent fabrication guide pin 90, therefore surrounding the entire stent fabrication guide pin 90, including the bevel, thus creating a constricted area within baseplate matrix 110. Once stent fabrication guide pin 90 is removed from baseplate matrix 110, what remains is a cavity (not shown), which has a restricted area that is later, adjusted to control the tightness of movement of the pilot drill guide tube inside baseplate matrix 110. Baseplate matrix 110 is then shaped and polished, wherein baseplate matrix 110 becomes stent 120 as shown in FIG. 3H.

FIG. 3H shows stent 120 with pilot drill guide tube 100 placed in stent 120 and a pilot bone drill bit 152 placed within pilot drill guide tube 100 in patient's mouth 40. Stent fabrication guide pin 90 (as shown in FIG. 3G) has been removed from stent 120 and stent 120 has been cured, shaped, glazed and sterilized for patient use. Pilot drill guide tube 100 is placed in stent 120, preferably with a sharp end 104 (as shown in FIG. 7C) of pilot drill guide tube 100 placed first into a stent hole (not shown). Pilot drill guide tube 100 may be pushed into the stent hole (not shown) with a round burnisher or a glick 1 until pilot drill guide tube 100 first comes into contact with the bony ridge and then pushed slightly more until it becomes actively engaged with the bony ridge. Therefore, locking pilot drill guide tube 100 and stent 120 into place. This allows for secure drilling of pilot holes in patient's mouth 40. The dentist may prepare the stent hole (not shown) for pilot drill guide tube 100 by using a round bur to adjust the constricted resin area created from the bevel in the stent fabrication guide pin. The dentist can adjust the tension placed on pilot drill guide tube 100 as needed to position and moveably control pilot drill guide tube 100.

In another embodiment before the dentist places pilot drill guide tube 100 into stent 120. The dentist may place the stent fabrication guide tube into stent 120 on the day of surgery, wherein the dentist pushes and turns the stent fabrication guide tube through the stent hole into gingival tissue 51 creating a bleeding spot 52 (as shown in FIG. 6L) within patient's mouth 40. Stent 120 is then removed from patient's mouth 40 and gingival tissue 51 is removed in and around the bleeding spot with a diamond bur, tissue punch drill or tissue forceps.

In another embodiment stent 120 is cured, shaped, glazed and sterilized as described above in FIG. 3H, however after gingival tissue 51 has been removed stent 120 is placed back in patient's mouth 40 without pilot drill guide tube 100 in place. In this embodiment, round bur drill bit 152 is placed in the stent hole and a shallow penetration hole 138 (as shown in FIG. 6F) is made in the top of the bony ridge.

Figure 6A:
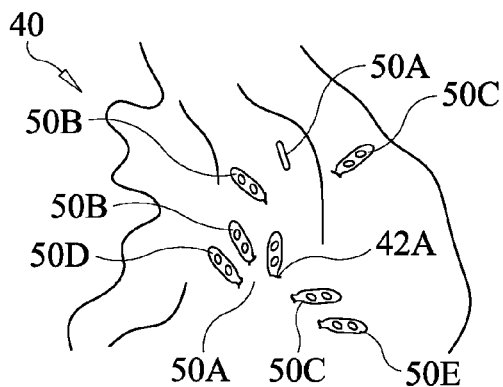
FIG. 6A shows the patient's mouth with multiple gingival depth impression pins inserted into the gingival tissue at the implant sites.
Figure 6B:
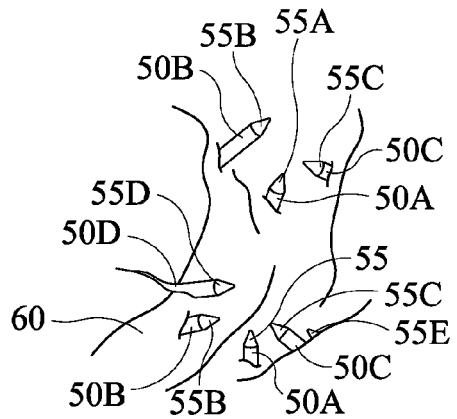
FIG. 6B shows the impression with all the gingival depth impression pins in place.
Figure 6C:
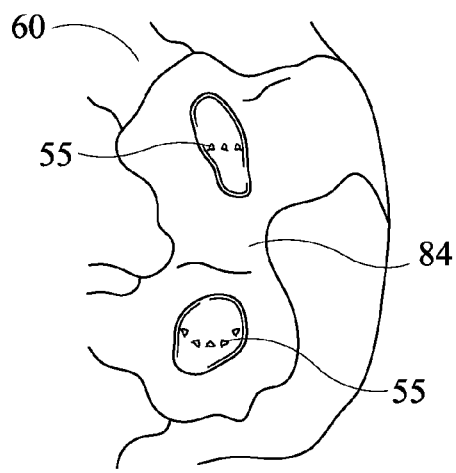
FIG. 6C shows artificial gingival tissue molded into the impression and shaped around the penetration ends of the gingival depth impression pins.
Figure 6D:
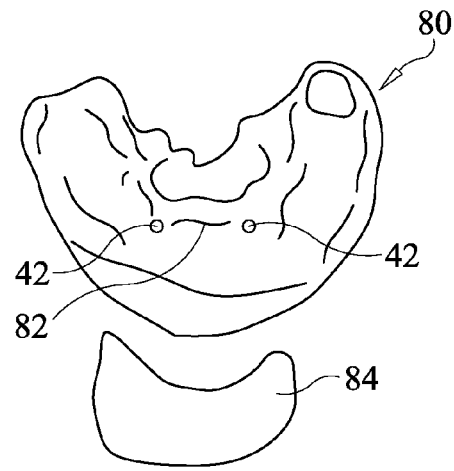
FIG. 6D shows the working model with the artificial gingival tissue removed.
Figure 6E:
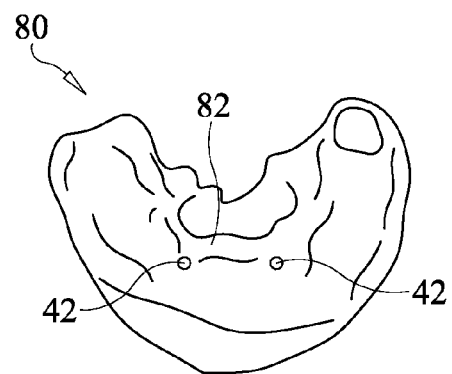
FIG. 6E shows a top view of the working model.
Figure 6F:
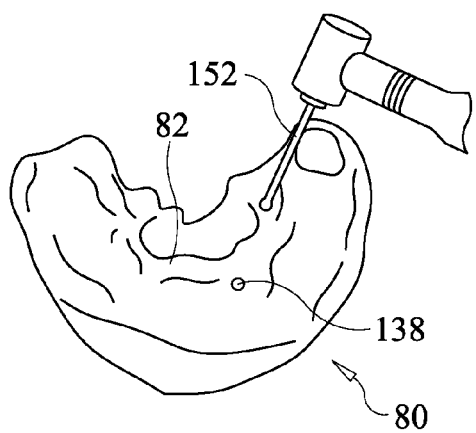
FIG. 6F shows the working model about to be drilled with a round bur.
Figure 6G:
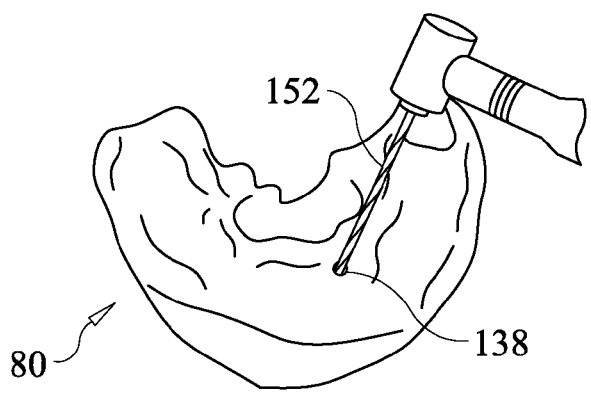
FIG. 6G shows pilot holes being made with a pilot bone drill bit.
Figure 6H:
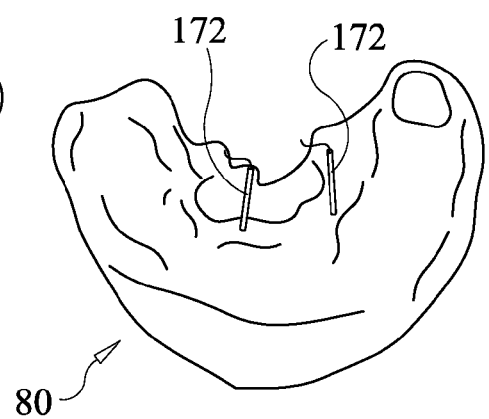
FIG. 6H shows stent fabrication guide wires placed inside the pilot holes.
Figure 6I:
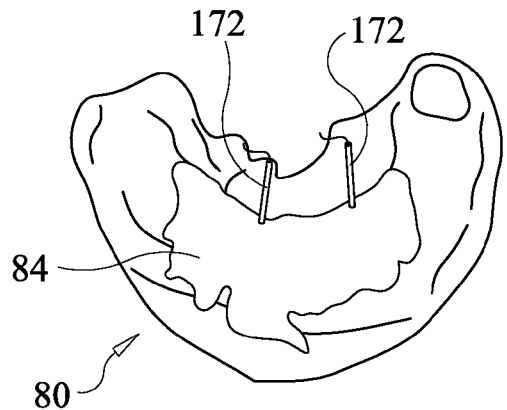
FIG. 6I shows the artificial gingival tissue placed back over the stent fabrication guide wires.
Figure 6J:
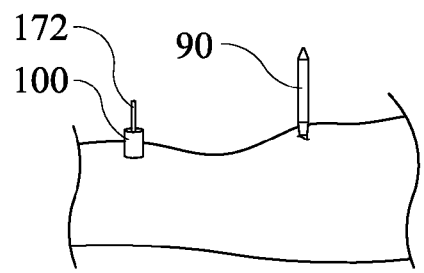
FIG. 6J shows a pilot drill guide tube placed over the stent fabrication guide wires on left and a stent fabrication guide pin on right.
Figure 6K:
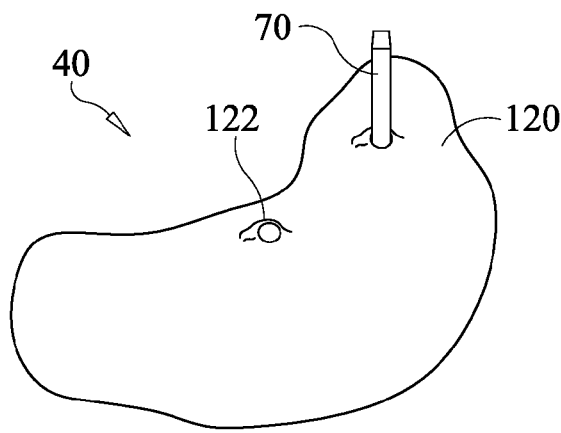
FIG. 6K shows the stent positioned in the patient's mouth on the day of surgery with the stent fabrication guide tube placed in the stent.
Figure 6L:
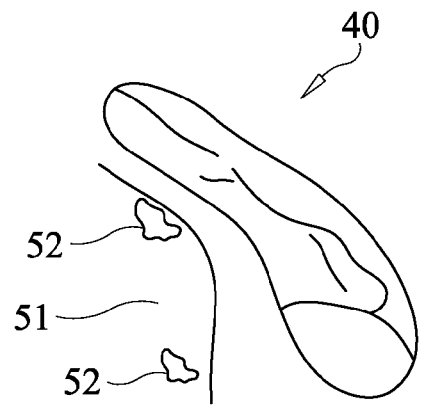
FIG. 6L shows bleeding spots within the patient's mouth.
Figure 6M:
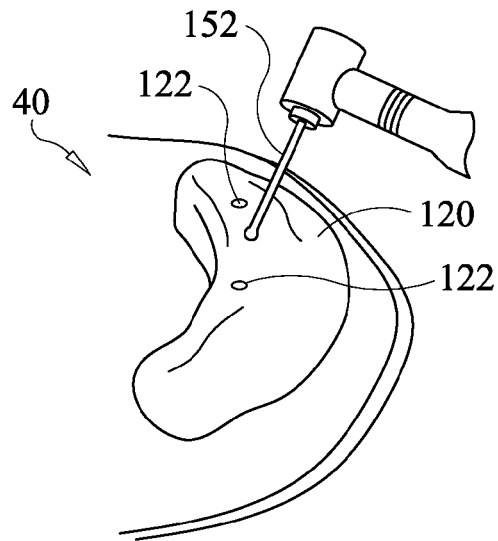
FIG. 6M shows the stent in the patient's mouth with a round bur bit about to be placed into the stent.
Figure 6N:
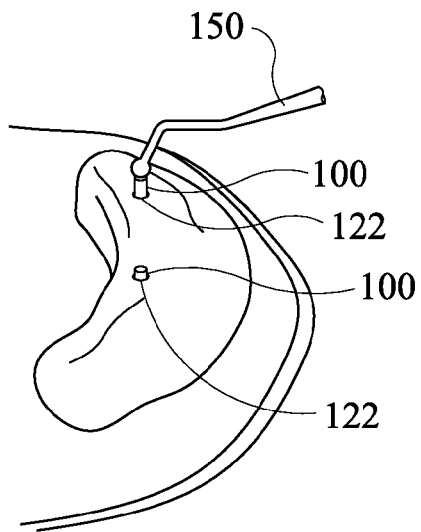
FIG. 6N shows pilot drill guide tubes placed within the stent holes using a dental instrument.
Figure 6O:
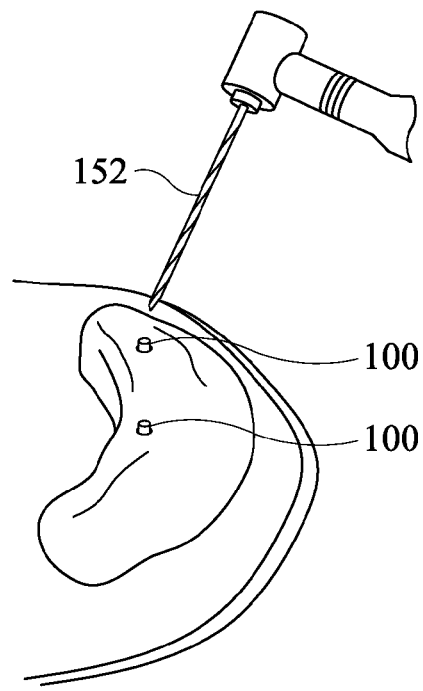
FIG. 6O shows the pilot holes being made with the pilot bone drill.
Figure 6P:
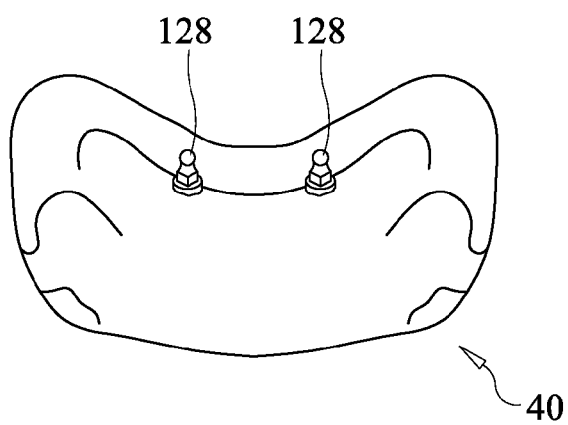
FIG. 6P shows the implant bodies placed within the pilot holes inside the patient's mouth.

On the day of surgery pilot bone drill bit 152 may be inserted into pilot drill guide tube 100, wherein pilot bone drill bit 152, drills a hole in the penetration site, and an implant body 128 (as shown in FIG. 6P) may be placed as will become apparent as the description proceeds.

FIGS. 4A-4D shows another embodiment, more specifically the fabrication of a driver stent and the day of surgery using the driver stent.

Figure 4A:
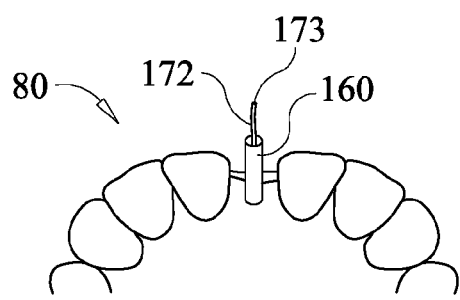
FIG. 4A shows a stent fabrication guide wire and a driver stent fabrication barrel placed in the working model.
Figure 4B:
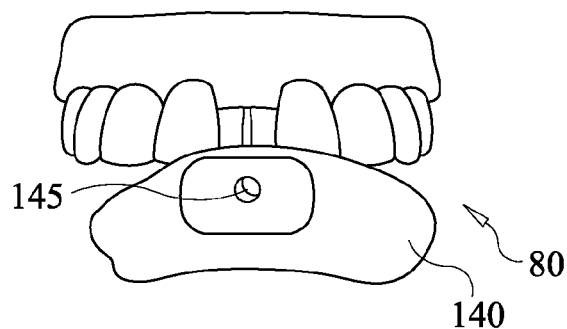
FIG. 4B shows a finished implant driver stent, which has a hole.

FIG. 4A shows a stent fabrication guide wire 172 and a driver stent fabrication barrel 160 placed in working model 80. A driver stent 140 (as shown in FIG. 4B) can be made off of working model 80 as shown in FIG. 3E, wherein stent fabrication guide wire 172 is placed within the stent fabrication guide tube and driver fabrication barrel 160 is placed over stent fabrication guide wire 172 and the stent fabrication guide tube. Stent fabrication guide wire 172 has a first end 171 and a second end 173 (as shown in FIG. 7D), wherein both ends 171, 173 have a sharp point. The preferred dimensions of stent fabrication guide wire 172 are a diameter that matches the outside diameter of the pilot drill bit being used and a length approximately 35 mm long. Stent fabrication guide wire 172 may be made of high-grade 304 stainless steel stock. Driver stent fabrication barrel 160 preferred dimensions may vary but a length of 13 mm to 15 mm is usually appropriate. Driver stent fabrication barrel 160 has an inside diameter, which matches the diameter of the pilot drill bit being used and an outside diameter, which matches the diameter of an implant driver.

FIG. 4B shows the working model with a finished implant driver stent, which has a hole. The driver stent fabrication barrel creates hole 145 during the formation of driver stent 140 in working model 80. The procedure to make driver stent 140 is the same procedure as described above in FIGS. 3G & 3H.

Figure 4C:
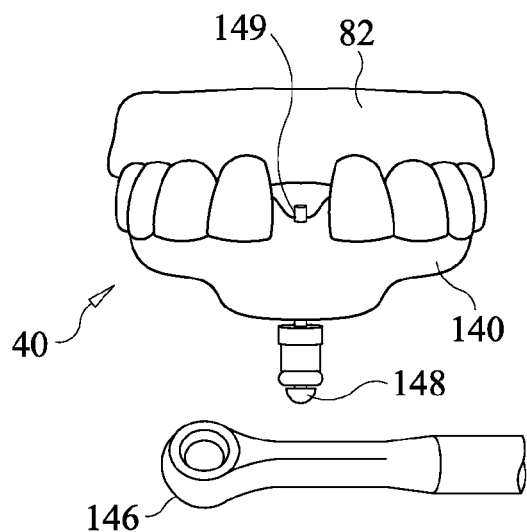
FIG. 4C shows a driver stent placed in the patient's mouth with an implant driver and a wrench.

FIG. 4C shows the driver stent placed in the patient's mouth with an implant driver and a wrench. Driver stent 140 is placed in patient's mouth 40 on the day of surgery over the area where an implant is to be placed during surgery. An appropriate sized implant driver 148 is chosen and placed in hole 145 as shown in FIG. 4B and wrench 146 is used to screw implant 149 into bony ridge 82.

Figure 4D:
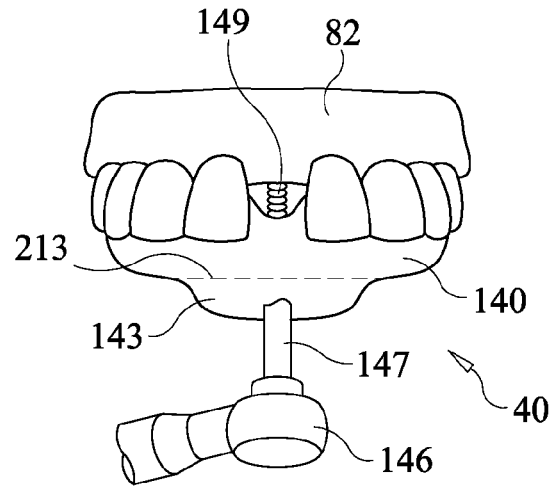
FIG. 4D shows the implant being driven into the patient's mouth using a wrench and an implant driver.

FIG. 4D shows an implant 149 being driven into patient's mouth 40 using wrench 146 and a driver 147. Driver 147 drives implant 149 into bony ridge 82. Driver stent 140 has an extension 143, which is shown by a dashed line 213 for clarity. Extension 143 provides more guidance in keeping implant 149 in line and straight. Therefore, allowing implant 149 to be in the desired position in bony ridge 82. The dentist predetermined the desired position during case workup diagnostic and planning procedures. Once implant 149 is in place a premade crown (not shown) may be placed over implant 149, thus completing the surgery. It should be noted that driver stent 140 is used when the dentist uses a self-taping implant as self-taping implants will follow a pilot drill hole until; the self-taping implant comes into contact with a bone area, which is less dense. The self-taping implant will then follow this "new" path and not be correctly aligned in bony ridge 82.

FIGS. 5A-5E show the surgical protocol of the completed stent.

Figure 5A:
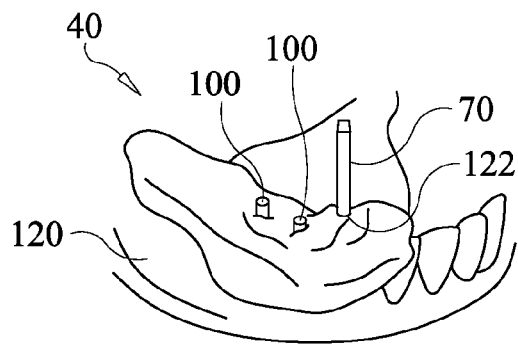
FIG. 5A shows as an example the surgical protocol for a three (3) implant stent with two (2) pilot drill guide tubes and one (1) stent fabrication guide tube inside the patient's mouth.

FIG. 5A shows as an example the surgical protocol for a three (3) implant stent with two (2) pilot drill guide tubes and one (1) stent fabrication guide tube inside the patient's mouth. Stent fabrication guide tube 70 is located in stent hole 122 and is pressed against the gingival tissue, thus creating the bleeding spot. Next, stent fabrication guide tube 70 and stent 120 will be removed from patient's mouth 40, therefore allowing the dentist to remove the gingival tissue with dental forceps located at the bleeding spots. Stent 120 is then placed back in patient's mouth 40 and the round bur drill bit is placed into stent hole 122, wherein the round bur dill bit penetrates the bony ridge a few millimeters where the gingival tissue was removed.

Figure 5B:
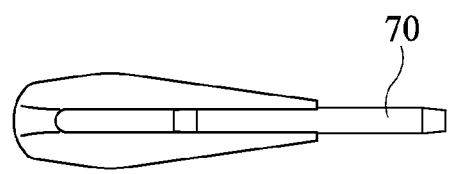
FIG. 5B shows a stent fabrication guide tube.

FIG. 5B shows the stent fabrication guide tube held by forceps. Stent fabrication guide tube 70 is cut at a length determined by the dentist, thus creating two (2) pilot drill guide tubes. The pilot drill guide tubes preferred length is between 8 and 15 mm long. The dentist may adjust the length of the pilot drill guide tubes for each implant site based on the pilot hole depth requirements and the length of the drill bit being used. The pilot drill guide tube has an inside diameter and an outside diameter. These diameters will vary depending on the diameter of the pilot bone drill bit being used. However, the inside diameter of the pilot drill guide tube is preferably a few thousands of a millimeter larger than the pilot bone drill bit so as to allow for free turning of the pilot bone drill bit, but not so large as to allow the pilot bone drill bit to "wobble" inside the pilot drill guide tube.

Figure 5C:
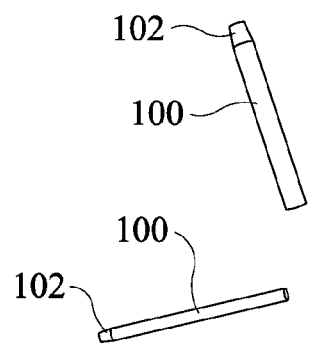
FIG. 5C shows the pilot drill guide tubes.

FIG. 5C shows the pilot drill guide tubes. Pilot drill guide tubes 100 have a beveled end 102, which is placed into the stent hole. Stent 120 as described in FIG. 3G has a constricted area, which will hold pilot drill guide tube 100 tightly in the stent.

Figure 5D:
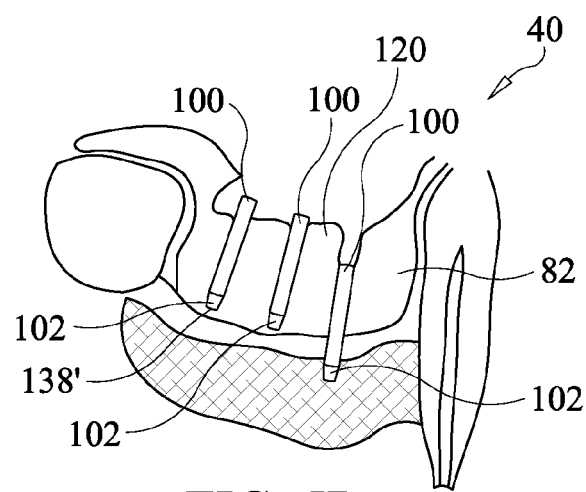
FIG. 5D shows the patient's mouth with the stent in place and one pilot drill guide tube actively engaged in the bony ridge.

FIG. 5D shows the patient's mouth with the stent in place and one of the pilot drill guide tubes actively engaged in the bony ridge. As can be seen stent 120 has a curvature, which fits around the gingival tissue in patient's mouth 40 and pilot drill guide tube 100 is forced through the constricted area of stent 120. Beveled end 102 of pilot drill guide tube 100 engages bony ridge 82 at the location of penetration hole 138. By engaging pilot drill guide tube 100 with bony ridge 82 it allows for maximum directional control. The engaged pilot drill guide tube 100 prevents the drill bit from going off line and accidentally sliding down drilling outside the surface of bony ridge 82. It should be noted that stent 120 abuts against gingival tissue 51 (as shown in FIG. 3H) and fits tightly against the adjacent teeth. It should be noted that pilot drill guide tubes 100 may extend substantially beyond stent 120 as shown in FIG. 5A. Generally, however, pilot drill guide tubes 100 or stent fabrication guide tubes 70 can be flush or even with stent 120. However, it is within the scope of this claimed disclosure for pilot drill guide tubes 100 to be flush as shown in FIG. 5D or they can extend beyond stent 120 as shown in FIG. 5A.

Figure 5E:
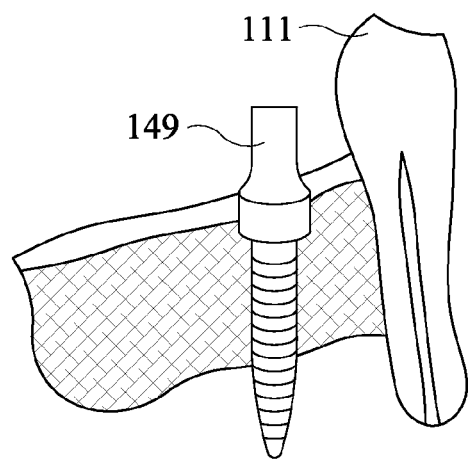
FIG. 5E shows the dental implant placed in the bony ridge.

FIG. 5E shows the dental implant placed in the bony ridge. As a result of using the stent, implant 149 is in perfect position; parallel to other teeth 111 and/or other implants 149. Implant 149 is placed into the pilot hole and driven into place as described above with the wrench having the driver attached to the wrench. Once implant 149 is in position the crown may be connected to implant 149.

FIGS. 6A-6P shows the procedure for a multiple implant case.

FIG. 6A shows the patient's mouth with multiple gingival depth impression pins inserted into the gingival tissue at the implant sites. Gingival depth impression pin 50A marks the position of penetration site 42A where the pilot hole will later be drilled. Gingival depth impression pins 50B, 50C immediately next to gingival depth impression pin 50A mark edges and corners of the bony ridge in patient's mouth 40. Gingival depth impression pins 50D, 50E farthest from gingival depth impression pin 50A mark the shape of the bony ridge farthest down, which allows the dentist to have a better understanding of the shape of the bony ridge. An impression is then taken of patient's mouth 40 with gingival depth impression pins 50A-E still in place as described in FIG. 3A. Also, recovery cord 57 (as shown in FIG. 3A) is placed through the impression retention end, allowing the dentist to pull gingival depth impression pins 50A-E out of the impression, once the dentist is done using the impression to mold working model 80 (as shown in FIG. 6D).

FIG. 6B shows the impression with all the gingival depth impression pins in place. Impression 60 is removed from the patient's mouth, which reveals penetration ends 55 A-E of gingival depth impression pins 50 A-E. Exposed penetration ends 55 A-E of gingival depth impression pins 50 A-E represents the depth and shape of the gingival tissue at the penetration site in the patient's mouth.

FIG. 6C shows artificial gingival tissue 84 molded into impression 60 and shaped around the penetration ends of the gingival depth impression pins. Artificial gingival tissue 84 gives the dentist a representation of the depth of the gingival tissue. Artificial gingival tissue 84 is then set with artificial ultra violet light. Dental stone is then poured into the impression, wherein the dental stone is hardened and removed from the impression creating working model 80 (as shown in FIG. 6D) for the dentist.

FIG. 6D shows the working model with the artificial gingival tissue removed. Artificial gingival tissue 84 is removed revealing the anatomy of bony ridge 82 at penetration sites 42 in working model 80.

FIG. 6E shows a top view of the working model. With the artificial gingival tissue removed the dentist is able to see the width of bony ridge 82 at penetration sites 42 in working model 80.

FIG. 6F shows the working model about to be drilled with the round bur drill bit. With the artificial gingival tissue removed, the dentist is able to see bony ridge 82 in working model 80 easier. This allows for the dentist to make penetration holes 138 in the desired spot on working model 80 using round bur drill bit 152.

FIG. 6G shows the pilot holes being made with the pilot bone drill bit. Pilot drill bit 152 is placed in penetration holes 138, wherein pilot drill bit 152 is adjusted to be at the proper drilling angle and the pilot holes are made for each of the implant sites in working model 80.

FIG. 6H shows the stent fabrication guide wires placed inside the pilot holes. Stent fabrication guide wires 172 are first cut and then placed in pilot holes 121, the sharp end of stent fabrication guide wires 172 projecting outward from working model 80.

FIG. 6I shows the artificial gingival tissue placed back over the stent fabrication guide wires. Artificial gingival tissue 84 is placed back into position over stent fabrication guide wires 172. Artificial gingival tissue 84 is pressed down over stent fabrication guide wires 172 until stent fabrication guide wires 172 create a hole (not shown) in artificial gingival tissue 84. The pilot bone drill bit may also be used to enlarge the hole in artificial gingival tissue 84 if needed. Stent fabrication guide wires 172, which were first cut are removed from working model 80 and replaced with full-length stent fabrication guide wires 172. The full-length stent fabrication guide wires 172 have a preferred length of 35 mm. The dentist then compares stent fabrication guide wires 172 to see how parallel the pilot holes (not shown) were made in working model 80. If the pilot holes are not parallel then the dentist may correct the pilot holes or bend stent fabrication guide wires 172 until all stent fabrication guide wires 172 are parallel with each other.

FIG. 6J shows the pilot drill guide tube placed over the stent fabrication guide wire and the stent fabrication guide pin. The stent fabrication guide wire with pilot drill guide tube 100 may be used or the stent fabrication guide wires may be removed and replaced with stent fabrication guide pin 90. Either pilot drill guide tube 100 over stent fabrication guide wire 172 or stent fabrication guide pin 90 may be used to make the stent. It should be noted that pilot drill guide tube 100 or stent fabrication guide pin 90 may also be aligned staggered, rather than being aligned in a straight line. Aligning multiple posterior MDI's when replacing multiple teeth in a staggered manner (rather than a straight line) provides additional support from buccal lingual forces. This advantage allows for the fabrication of wider (buccal-lingual) crowns, for increased chewing power (a larger occlusal table) and more natural looking teeth. Once the dentist has decided on the type of layout, then the baseplate matrix is molded around and inside either pilot drill guide tube 100 or stent fabrication guide pin 90 with either a dental instrument such as the Hollandbeck or the dentist's fingers. The baseplate matrix is then shaped, polished and sterilized, therefore becoming stent 120 (as shown in FIG. 6K).

FIG. 6K shows the stent positioned in the patient's mouth on the day of surgery with the stent fabrication guide tube placed in the stent. On the day of surgery, the patient is anesthetized and stent 120 is sterilized and placed in patient's mouth 40. Stent fabrication guide tube 70 is pushed and turned in a downward motion through stent hole 122 into the gingival tissue creating the bleeding spot within patient's mouth 40. Stent 120 is then removed from patient's mouth 40.

FIG. 6L shows bleeding spots within the patient's mouth. Stent 120 is removed, revealing bleeding spots 52 within patient's mouth. 40. Gingival tissue 51 is removed from bleeding spots 52 with either a diamond bur, tissue punch bur or tissue forceps.

FIG. 6M shows the stent in the patient's mouth with the round bur bit about to be placed into the stent. Stent 120 is sterilized and placed back into patient's mouth 40. Round bur bit 152 is placed into each stent hole 122 and the penetration holes are made 1mm into the bony ridge.

FIG. 6N shows the pilot drill guide tubes placed within the stent holes using the dental instrument. Pilot drill guide tubes 100 are placed into each stent hole 122. Dental instrument 150 such as a round burnisher or a glick 1 is used to push pilot drill guide tube 100 into the penetration holes. The dentist continues to push until pilot drill guide tube 100 first comes into contact with the bony ridge. Pilot drill guide tube 100 is then pushed slightly more until it becomes actively engaged with the bony ridge inside the penetration holes. This locks pilot drill guide tube 100 and stent 120 into place allowing the dentist to securely drill the pilot holes.

FIG. 6O shows the pilot holes being made with the pilot bone drill. Pilot drill bit 152 is placed into pilot drill guide tube 100, wherein the dentist drills into the bony ridge creating the pilot holes.

FIG. 6P shows the implant bodies placed within the pilot holes inside the patient's mouth. Before implant bodies 128 are placed within patient's mouth 40 an appropriate intermediate bone drill is used to slightly widen the pilot holes. Implant body 128 is then placed within the pilot holes according to implant manufacturers instructions and protocols.

FIG. 7A shows the stent fabrication guide tube having a first end and a second end. Stent fabrication guide tube 70 has a first end 72 and a second end 74, with each end 72, 74 being beveled. The bevel, has an outside diameter 76 and an inside diameter 78, wherein outside diameter 76 is larger than inside diameter 78, thereby outside diameter 78 tapers towards inside diameter 76. Inside diameter 78 has a sharp cutting edge, wherein when force is applied to stent fabrication guide tube 70, inside diameter 78 is capable of creating the bleeding spot on the gingival tissue as well as actively engaging with the bony ridge. The preferred length of stent fabrication guide tube 70 is approximately 21 mm long. Stent fabrication guide tube 70 may be cut in half to become two pilot drill guide tubes of lengths desired by the attending dentist. Stent fabrication guide tube 70 is used both in laboratory stent fabrication procedures and in Surgical Protocols. When stent fabrication guide tube 70 is cut in half stent fabrication guide tube 70 can be used to make the stent in the laboratory protocol. Stent fabrication guide tube 70 may also be placed over the stent fabrication guide wire with inside diameter 78 of stent fabrication guide tube 70 located towards the working model, thereby creating a resin constriction in the baseplate matrix. When stent fabrication guide tube 70 is used in it's long uncut version it is used during surgery to mark the gingival tissue, which creates the bleeding spot and marks the gingival tissue to be removed at the penetration site. Stent fabrication guide tube 70 may also be used in laboratory protocol to "work the constriction" in the stent. Stent fabrication guide tubes 70 can be made from any suitable non-toxic materials, metal or plastic such as stainless steel, metal alloys, or any other suitable materials available to those of ordinary skill in the art.

FIG. 7B shows the stent fabrication guide pin. Stent fabrication guide pin 90 has a length, shape and outside diameter designed to work in unison with surgical length dental drills, as well as the stent fabrication guide tube and the pilot drill guide tube. Stent fabrication guide pin 90 has larger outside diameter 94 and smaller outside diameter 96. Larger outside diameter 94 is used to create the hole in the baseplate matrix that the surgical length dental drill will later work inside of, while smaller outside diameter 96 is of an approximate diameter to firmly enter and engage the penetration site of the working model. In the middle of stent fabrication guide pin is bevel 92, which creates an area of constricted resin in a inferior surface of the baseplate matrix, which keeps the pilot drill guide tube tight in the baseplate matrix during surgery. Bevel 92 also "locks" stent fabrication guide pin 92 during the baseplate matrix molding procedure of the stent. Many materials may be used, such as stainless steel, titanium alloy, and various other alloys available to dentistry and medicine.

FIG. 7C shows the pilot drill guide tube. Pilot drill guide tube 100 has a preferred length between 8 and 15mm long. The dentist may adjust the length of pilot drill guide tubes 100 for each implant site based on the pilot holes depth requirements and the length of the drill bit being used. The dentist may cut the stent fabrication guide tube in half to make two (2) pilot drill guide tubes 100. Pilot drill guide tube 100 has an inside diameter 109 and an outside diameter 106. The diameters 106 may vary depending on the diameter of the pilot bone drill bit being used for the procedure. The inside diameter (not shown) will be a few thousands of an inch larger than the outside diameter of the pilot bone drill bit, so as to allow free turning of the pilot bone drill bit to minimize excessive friction, but not so large as to allow the pilot bone drill bit to "wobble" inside pilot drill guide tube 100. Pilot drill guide tube 100 has an external bevel 102 and an internal bevel (located inside the pilot drill guide tube and not shown). External bevel 102 has an outside diameter 103 a few millimeter's from the end of pilot drill guide tube 100. Bevel 102 ends at end 104, forming a sharp cutting edge which is defined by the inside diameter 104 of pilot drill guide tube 100. At the opposite side of pilot drill guide tube 100 is the internal bevel (not shown), wherein the bevel starts on the inside surface of the pilot drill guide tube a few millimeter's from the end of end 108, which is defined by outside diameter 106 of pilot drill guide tube 100. This reversed bevel allows for easier and quicker entrance of the pilot bone drill bit into pilot drill guide tube 100 during surgery. The main function of pilot drill guide tube 100 is to interface with the pilot bone drill bit and to keep the drill bit on the pre-established correct path as the drill bit enters the bony ridge. Proper fabrication of the stent allows for movement of pilot drill guide tube 100 inside the stent, wherein this movement allows pilot drill guide tube 100 to move along a long axis of the stent hole and thereby allows pilot drill guide tube 100 to be moved to engage the surface of the bony ridge.

FIG. 7D shows the stent fabrication guide wire. Stent fabrication guide wire 172 has a preferred length of approximately 35 mm and has the same diameter as the pilot bone drill bit being used. Stent fabrication guide wire has two ends 171, 173, with each end 171, 173 having a sharp point. Stent fabrication guide wire 172 is utilized at full length for stent fabrications and is placed in the pilot holes of the working model to check for parallelism of multiple implants. This is particularly important when placing two (2) or more implants for overlay dentures. Stent fabrication guide wire 172 may be cut in half to custom lengths as desired by the doctor for the "lost gingival technique" procedure. The part of stent fabrication guide wire 172, which is cut is placed into the pilot holes of the working model, with the sharp point end 171, 173 protruding outward. Sharp end 171, 173 allows stent fabrication guide wire 172 to penetrate the artificial gingival tissue, therefore creating holes in the proper positions required for stent fabrication. Stent fabrication guide wire 172 is manufactured to very tight tolerances. Stent fabrication guide wire 172 may also be utilized in the same way as the gingival depth impression pin as described above. In this embodiment stent fabrication guide wire 172 is cut at length determined by following the bone sounding procedure described above. Once stent fabrication guide wire 172 has been cut to the proper length it is placed inside the impression before applying the artificial gingival tissue.

FIG. 7E shows the gingival depth impression pin. Gingival depth impression pin 50 has penetration end 53 and impression retention end 55. Penetration end 53 is in the shape of a pin or a cuneated or wedge-shaped point, capable of penetrating the patient's gingival tissue. Penetration end 55 has a diameter the same as the pilot drill bit. Penetration end 53 may also have horizontal cuts or ridges, which create retention when pushed into the gingival tissue. This retention in the gingival tissue creates a "tug back" when the gingival depth impression pin is removed from the gingival tissue. Impression retention end 55 is of a geometry that allows for the attachment of recovery cord 57, a piece of dental floss, or other retentive elements, which allow for an impression material to grab during the removal of the impression. The geometry of impression retention end 55 may be of a shape, having a flat rectangular end with small holes 59 within the flat rectangular shape, which are capable of receiving recovery cord 57 as well as having a retentive element. Impression retention end 55 may be of a circular shape such as in the shape of an eye hook which is capable of receiving recovery cord 57 as well as having a retentive element. Additionally, gingival depth impression pin 50A (as shown in FIG. 6A) in the procedure for a multiple implant case as described above, may be used to stabilize the stent fabrication guide tube when the artificial gingival tissue is set up inside the impression.

Figure 7F:
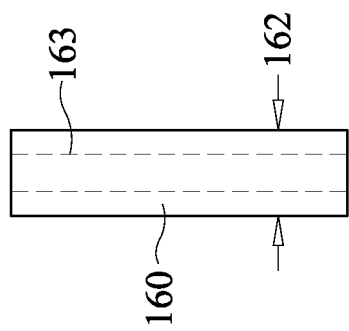
FIG. 7F shows a driver stent fabrication barrel.
Figure 7E:
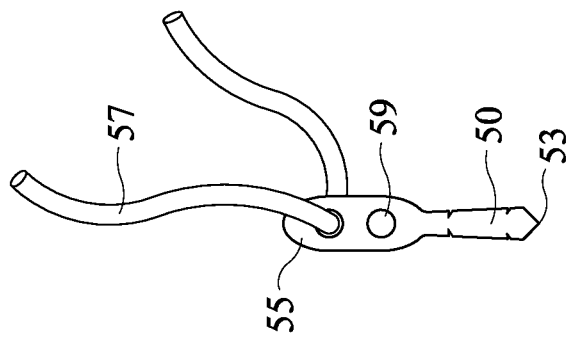
FIG. 7E shows a gingival depth impression pin.
Figure 7D:
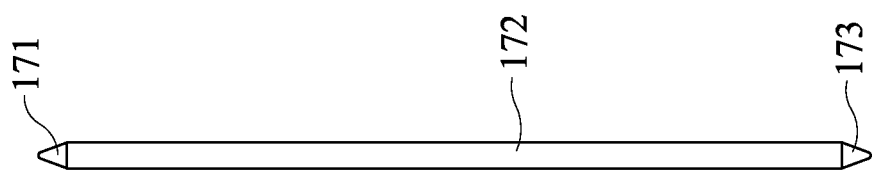
FIG. 7D shows a stent fabrication guide wire.

FIG. 7F shows the driver stent fabrication barrel. Driver stent fabrication barrel 160 is used to make the driver stent that guides the dental implant to its proper position. This is important when an "Immediate Load" protocol is used when placing dental implants, i.e., when the dentist places a pre-made crown on the implant body the same day as implant surgery. Driver stent fabrication barrel 160 has an outside diameter 162, which is the same diameter as the "driver" or wrench adapter commonly used by dentists when using a narrow diameter implant. Driver stent fabrication barrel 160 has a length of 13 to 15 mm and inside diameter 163 (represented by hidden lines) matches the outside diameter of the pilot drill bit being used. Using the same working model as used in making the stent, driver stent fabrication barrel 160 is placed on the stent fabrication guide wire and the driver stent is created as described above. The results in using the driver stent is the driver stent has the same precision for placing dental implants as the stent was for creating pilot holes. Therefore, the driver stent keeps self-taping one piece implants in the correct position and path when the dental implant is driven into the bony ridge, making the procedure more precise and easier to cement a pre-made crown.

The baseplate matrix (as shown in FIG. 3G) may comprise of any suitable plastic non-toxic material such as a standard dental acrylic or others including silicone-based materials, vacuum-formed stent materials, computer driven lithograph technique materials, or other materials available to those of ordinary skill in the art.

It should be noted that gaining initial stabilization of the one-piece or multiple implant bodies upon placement of that implant body inside the patient's bony ridge is paramount for successful integration of the implant body. The method used to accomplish this task especially in bony ridges of less than optimal density, is using the bone engaging dental implant surgical stent placement system, wherein the general procedure is initially followed, with first being the fabrication of the stent, which comprises of first placing the gingival depth impression pin in the patient's mouth at the preferred penetration site. The gingival depth impression pin is pushed until it comes into contact with the bony ridge. Next, the dentist takes the impression of the patient's mouth using dental impression material. The dentist then will remove the impression with the gingival depth impression pins also in the impression from the patient's mouth, wherein inside the impression reveals the penetration end of the gingival depth impression pin. It should be noted that the exposed penetration end of the gingival depth impression pin represents the depth of the patient's gingival tissue at the penetration site in the patient's mouth. Next, the dentist may apply the artificial gingival tissue to the inside of the impression around the gingival depth impression pin. The proper thickness of the artificial gingival tissue is also based on the measurements observed when the dentist performs "bone sounding" of the patient's bony ridge at the penetration site. Afterwards, the dentist places the stent fabrication guide tube over the gingival depth impression pin and then pours dental stone into the impression to create the working model. Once the dental stone has hardened, the dentist may remove the artificial gingival tissue from the working model, thus revealing a three dimensional (3D) representation of the patient's bony ridge. It is at this time that the dentist may make necessary adjustments at the penetration site such as changing the penetration hole position on the bony ridge, as well as changing the angle of the pilot hole. Once any necessary adjustments are made, the dentist places the artificial gingival tissue back on the working model and places the stent fabrication guide pin into the hole of the working model, where the penetration site was formed. Next, the dentist should use a soft baseplate matrix preferably light cured baseplate resin, which is molded around the stent fabrication guide pin and over the adjacent teeth. The dentist may use such dental instruments as the Hollandbeck or fingers to force the baseplate matrix around the stent fabrication guide pin and into the stent fabrication guide pin bevel. Lastly, the baseplate matrix is cured, shaped, glazed and sterilized, which results in the baseplate matrix transforming into the stent. If upon completion of the stent the dentist believes that the stent fabrication guide pins position is questionable the working model will be sectioned near the stent fabrication guide pin where its position and direction in the working model will be observed. If the stent fabrication guide tube or pilot drill guide tube is out of position then the stent fabrication guide tube will be luted in the proper position and the working model will be luted back together and a transfer stent will be fabricated. Next, the transfer stent will be placed on the working model and the corrected pilot holes will be drilled. Next, the stent fabrication guide pins are replaced and the transfer stent is fabricated as described above. The pilot drill guide tube may be placed in the stent and the constricted area of the resin is adjusted for pilot drill guide tube tightness. At this point the dentist may decide that if the case has a sufficient degree of difficulty that an Oral CT Scan be performed with the stent in place, for a final check of three-dimensional (3D) accuracy before the day of surgery. It should be noted that dentists new to the type of procedure described above may want to proceed with a dry run on a model of the patient's mouth before actually trying the above-described method on the patient's actual mouth.

The surgical protocol for the completed stent is as follows: the dentist will first have the patient anesthetized and then the dentist will place the sterilized stent into over the bony ridge and adjacent teeth of the patient. Pressure is applied to the stent creating first a circle marking caused by the contact of the stent fabrication guide tube or pilot drill guide tube. The dentist continues to apply pressure till the bleeding spot is created. Then the stent is removed from the patient's mouth and the gingival tissue in and around the bleeding spot is removed with a standard tissue punch or diamond bur or other suitable means used to remove small amounts of gingival tissue down to the bony ridge. The stent is then placed back in the patient's mouth and the round bur drill bit is used to penetrate the bony ridge a few millimeters where the gingival tissue was removed. Next, the pilot drill guide tube is forced through the constricted resin of the stent. The beveled end of the pilot drill guide tube engages the bony ridge in the previously drilled penetration hole, therefore providing active engagement with the bony ridge providing maximum stability of the stent and maximum directional control. It should be noted, by having the pilot drill guide tube actively engaged with the bony ridge it prevents the drill bit from going off line and accidentally sliding down, drilling outside the surface of the bony ridge. The stent should abut against the top of the patient's gingival tissue and fit tightly against the adjacent teeth. It also should be noted, that the pilot drill guide tubes may extend substantially beyond the stent. Generally, however, the pilot drill guide tubes can be flush or even with the stent. The pilot drill makes the pilot hole exactly where it needs to be in the bony ridge. This process is repeated until the pilot holes have been drilled for each of the pilot drill guide tubes in the stent. Obviously, every patient will be different so that the stent and the tube's length, etc. must be determined for each patient. Subsequently the driver stent with a wider hole as described below is used when seating the implant body in the bony ridge. The stent is then removed, the implant as described below is set to final position and the crown is cemented to the dental implant.

In another embodiment the driver stent may be fabricated in addition to the stent. The driver stent uses the same method and the same working model as described above. However, once the working model is hardened the dentist places the stent fabrication guide wire into the hole of the working model, where the penetration site was formed. Next, the dentist places a driver stent fabrication barrel over the stent fabrication guide wire. Subsequently, the dentist should use a soft baseplate matrix preferably an ultra violet activated resin, which is molded around the driver stent fabrication barrel and over the adjacent teeth. The dentist may use a dental instrument such as a Hollandbeck and fingers to force the baseplate matrix around the driver stent fabrication barrel. Lastly, the baseplate matrix is cured, shaped, glazed and sterilized, therefore becoming the driver stent. Next, the dentist will have the patient anesthetized and then the dentist will place the sterilized driver stent in the patient's mouth over the area where the implant is to be placed. An appropriate sized implant driver is chosen and placed in the driver stent. Next, the wrench is attached to the driver and the driver drives the implant into the bony ridge. The driver stent may be made a little higher in this case to provide early guidance in keeping the implant driver and implant in line and straight. Therefore, allowing the implant to be in the proper position in the patient's mouth. Once the implant is in place the dentist may place a premade crown over the implant, thus completing the surgery.

It should be noted that gaining initial stabilization in an edentulous case, which requires multiple implant bodies inside the patient's bony ridge is paramount for successful integration of the implant body. The method used to accomplish this embodiment especially in bony ridges of less than optimal density, is using the bone engaging dental implant surgical stent placement system. The general procedure is initially followed, with first being the fabrication of the stent, which comprises of first placing gingival depth impression pins in the patient's mouth at the preferred penetration site. Typically multiple gingival depth impression pins are inserted with the first gingival depth impression pin being inserted at the top of the bony ridge. This first gingival depth impression pin marks the desired position of the penetration hole. The dentist may then place additional gingival depth impression pins to mark the top edge corners of the bony ridge with additional gingival depth impression pins being placed further down the bony ridge, so that the dentist gets the most accurate representation of the patient's bony ridge. Next, the dentist takes an impression of the patient's mouth using the dental impression material. The dentist then will remove the impression with the gingival depth impression pins also in the impression from the patient's mouth, wherein inside the impression reveals the penetration end of the gingival depth impression pins. It should be noted that the exposed penetration end of the gingival depth impression pins represent the depth of the patient's gingival tissue at the penetration site in the patient's mouth. Also, by using multiple depth impression pins the dentist is also able to understand the general shape of the bony ridge. An appropriate dental material such as a pink soft reline material, is placed in the impression to replicate the thickness of the gingival tissue as determined by accurate bone sounding techniques as known in the art and as utilizing the described methods disclosed herein, therefore creating artificial gingival tissue. The balance of the impression is poured with standard dental model stone, plaster or other appropriate dental model material known in the art. Once the dental stone has hardened the impression is removed and the dentist is left with the working model including the artificial gingival tissue. The artificial gingival tissue is removed from the working model, therefore revealing the anatomy of the bony ridge at the penetration sites. The dentist by looking down on the model can notice the width of the bony ridge and determine the exact desired spots for the penetration holes in the working model. The pilot drill is placed at the penetration spots and adjusted for proper angle, and then the pilot hole is made for each implant site. Next, the stent fabrication guide wires are cut at a length desired by the dentist and placed in the pilot holes with the sharp end of the stent fabrication guide wires projecting outward, away from the working model. The artificial gingival tissue is then placed back over the working model and pressure is applied to the artificial gingival tissue, until the stent fabrication guide wires penetrate through the artificial gingival tissue. These penetration holes in the artificial gingival tissue represent the desired position for the pilot holes. The dentist next checks the stent fabrication guide wires to check and adjust for parallelism. Any minor parallelism issues may be corrected by gently bending the stent fabrication guide wires. This may be done without major consequences especially in a mesial or distal direction. It should be noted that this step is important because if the guide wires are not parallel then the pilot drill guide tubes in the stent will not be parallel, which will make is very difficult to place the dental implants parallel to each other in the patient's bony ridge. Once the dentist is satisfied with the parallelism of the stent fabrication guide wires the dentist may then place either the pilot drill guide tubes over the stent fabrication guide wires or replace the stent fabrication guide wires with stent fabrication guide pins. Next, the dentist should use a soft baseplate matrix, which is molded around the stent fabrication guide pins or pilot drill guide tubes and over the adjacent teeth. The dentist may use a dental instrument such as a Hollandbeck and fingers to force the baseplate matrix around the stent fabrication guide pins or stent fabrication guide tubes. Lastly, the baseplate matrix is cured, shaped, glazed and sterilized, therefore becoming the stent. Utilizing the "Proceed and Verify" protocol, the dentist verifies the pilot drill guide tubes proper positioning by taking x-rays and probing with a dental explorer, which will insure later the success of pilot hole creation. Before surgery the dentist may check to see if the holes in the stent are miss-angled. One way the dentist may check this, is to place the stent on a second working model and drill properly angled pilot holes. The second working model may then be cut at each pilot hole to check for accuracy and whether the angle is correct. If the holes in the stent are miss-angled the dentist may drill out a sufficient amount of baseplate matrix material to allow the dentist to re-angle and replace the stent fabrication guide wire in the pilot hole and place a new stent fabrication guide tube or pilot drill guide tube over the stent fabrication guide wire. The angle of the stent fabrication guide tube or pilot drill guide tube is then checked and the hole is re-cored with new baseplate matrix material and the stent is then recurred with ultraviolet light. At this point the dentist may also decide that if the case has a sufficient degree of difficulty that an Oral CT Scan be performed with stent in place, for a final check of three-dimensional (3D) accuracy before the day of surgery. It should be noted that dentists new to the type of procedure described above may want to proceed with a dry run on a model of the patient's mouth before actually trying the above described method on the patient's actual mouth.

On the day surgery the dentist will first have the patient anesthetized and then the dentist will place the sterilized stent into position. The stent fabrication guide tube is then placed into one of the holes in the stent, wherein the stent fabrication guide tube is pushed and turned in a downward motion through the stent and into the patient's gingival tissue, thus creating the bleeding spot. This process of creating the bleeding spot is continued until a bleeding spot is created for each hole in the stent. Once complete, the stent and the stent fabrication guide tubes are removed from the patient's mouth, therefore revealing the bleeding spots. The gingival tissue within the bleeding spots is removed with such dental instruments as a diamond bur, tissue punch drill or tissue forceps. The stent is then placed back into the patient's mouth and with the round bur drill bit the dentist places the drill bit in each hole and creates a shallow penetration hole in the top of the bony ridge. Pilot drill guide tubes of the proper length are then placed into the holes located in the stent with the sharp end of the pilot drill guide tube entering first. The pilot drill guide tube is then pushed through the stent hole and into the penetration hole until the pilot drill guide tube becomes actively engaged with the bony ridge. This locks the stent into place, which will allow for secure drilling of the pilot holes. This process of placing pilot drill guide tubes into place is repeated for each hole located in the stent. Once, all the pilot drill guide tubes are in place and actively engaged the dentist may take x-rays to check for proper positioning of all the elements. The dental explorer may also be used at this point to check all pilot drill guide tubes. The dentist will next select the appropriate size pilot drill bit and will pass the pilot drill bit through the pilot drill guide tubes and into the penetration hole. Next, the dentist will drill the appropriate sized pilot hole into the bony ridge. This process will be repeated until the dentist has drilled all the necessary pilot holes. Next, the dentist will removed the stent and the pilot drill guide tubes from the patient's mouth and select the appropriate intermediate bone drill bit. Once selected, the dentist will widen the pilot holes and the dental implants will then be placed into the pilot holes according to the implant manufacturer's instructions and protocols.

There are technical hurdles that need to be overcome in configuring and installing the Bone Engaging Dental Implant Surgical Stent Placement System, as disclosed herein. For example, those having skill in the art, such as dentists, will appreciate the fact that no current system or method exists that provides such precision at a cost, which is significantly lower than any other system, allowing more patients to afford the benefits of implant dentistry. Dentists will also appreciate that the following system provides a stent that is very stable, will not rock in any direction, which will provide maximum guidance and accurate placement of all pilot holes. Dentists will also appreciate that edentulous surgical stents will not require the drilling of additional holes along the vertical flanges, thus also not requiring the screwing in of "stent retaining" bone screws which were only used to keep the stent in a secure position, resulting in unnecessary trauma to the patient and additional post-operative pain and swelling. An additional benefit of the Bone Engaging Dental Implant Surgical Stent Placement System is the pilot drill guide tubes have the ability to bring sterile water directly to the bony ridge and the drill bit being used, keeping the bony ridge from heating and burning, which increases the chances for implant failure. Many pilot drills are too small for internal irrigation channels, therefore all implants, which require only one bone drill will immediately benefit from the stent of this invention. The tight interface between firm attached gingival tissue and the shaft of the pilot drill prevents irrigation from reaching the bone and the bone drill bit in other surgical stent systems. The surgical hand-pieces have external irrigation, but the path to the bone and the bone drill interface is further blocked by the large size of the prior art stents and is also encumbered by the directional devices' coverage of the surgical site in other implant surgical guide systems.

Although exemplary embodiments have been shown and described, it will be clear to those of ordinary skill in the art that a number of changes, modifications, or alterations to the disclosure as described may be made. For example, the stent fabrication guide tube or the pilot drill guide tube may be used interchangeably and they may also be used in certain instances instead of stent fabrication guide pins when making the stent on the working model. Another example is the number of missing teeth a patient's case presents or the number of implants planned or the type of dental prosthetics that are being placed on the implants all determine the general shape of the bone engaging dental implant surgical stent as well. All such changes, modifications, and alterations should therefore be seen as within the scope of the disclosure.

What is claimed is:

1. A bone engaging dental implant surgical stent placement procedure for providing a drill guide when making a pilot hole for an implant procedure in a bony ridge in the mouth of a patient, comprising:
   a gingival depth impression pin having a penetration end and an impression retention end to be placed in the patient's bony ridge at a location on the patient's gingival tissue to establish a penetration site, and
   an impression to be created of the patient's bony ridge by placing an impression material around the gingival depth impression pin and around the patient's gingival tissue, and having the impression removed from the patient's mouth, and placing a stent fabrication guide tube over the gingival depth impression pin, and pouring a dental stone into the impression surrounding the stent fabrication guide tube to create a working model with a penetration hole for placing a stent fabrication guide pin into the penetration hole, wherein the stent fabrication guide pin has a first outside diameter end, a second outside diameter end and a bevel and molding a baseplate matrix around the stent fabrication guide pin in the working model to create a bone engaging dental implant surgical stent which positions a pilot drill guide tube to actively engage with the bony ridge at the penetration site and to act as the drill guide when making the pilot hole, wherein the first outside diameter end of the stent fabrication guide pin is used to create a hole in the baseplate matrix when the baseplate matrix is molded around the stent fabrication guide pin, the second outside diameter end is of a diameter to firmly enter and engage the penetration site of the working model, the bevel is located in the middle of the stent fabrication guide pin, wherein the bevel creates an area of constricted resin in the baseplate matrix.

2. The bone engaging dental implant surgical stent placement procedure of claim 1, wherein the penetration end of the gingival depth impression pin has a shape of a pin capable of penetrating the patient's gingival tissue, the penetration end has a diameter the same as a drill bit, wherein the penetration end has horizontal ridges, which create retention when the penetration end is pushed into the gingival tissue.

3. The bone engaging dental implant surgical stent placement procedure of claim 1, wherein the impression retention end of the gingival depth impression pin is of a shape, having a flat rectangular end with small holes within the flat rectangular end, which are capable of receiving a recovery cord.

4. The bone engaging dental implant surgical stent placement procedure of claim 1, wherein the stent fabrication guide tube has a first end and a second end, wherein each end is of a shape of a bevel, the bevel has an outside diameter and an inside diameter, wherein the outside diameter tapers towards the inside diameter, the inside diameter has a sharp cutting edge, wherein when force is applied to the stent fabrication guide tube the inside diameter is capable of cutting the patient's gingival tissue and the inside diameter is capable of actively engaging with the bony ridge.

5. The bone engaging dental implant surgical stent placement procedure of claim 1, wherein the pilot drill guide tube has two ends and an inside diameter; the ends have of an external bevel located at one end and an internal bevel located at the other end, the external bevel tapers towards the end of the pilot drill guide tube to form a sharp cutting edge to allow the pilot drill guide tube to actively engage with the bony ridge, the internal bevel is a reversed bevel, which allows the pilot drill guide tube to act as the drill guide when making the pilot hole; the inside diameter is a few thousands of an inch larger than the drill bit, so as to allow the drill bit to freely turn.

6. A bone engaging dental implant surgical stent placement procedure for providing a drill guide when making a pilot hole for an implant procedure in a bony ridge in the mouth of a patient, comprising:

a gingival depth impression pin having a penetration end and an impression retention end to be placed in the patient's bony ridge at a location on the patient's gingival tissue to establish a penetration site, wherein the penetration end of the gingival depth impression pin have a shape of a pin capable of penetrating the patient's gingival tissue, the penetration end has a diameter the same as a drill bit, wherein the penetration end has horizontal ridges, which create retention when the penetration end is pushed into the gingival tissue, and an impression to be created of the patient's bony ridge by placing an impression material around the gingival depth impression pin and around the patient's gingival tissue, and having the impression removed from the patient's mouth, and placing a stent fabrication guide tube over the gingival depth impression pin, and pouring a dental stone into the impression surrounding the stent fabrication guide tube to create a working model with a penetration hole for placing a stent fabrication guide pin into the penetration hole, and molding a baseplate matrix around the stent fabrication guide pin in the working model to create a bone engaging dental implant surgical stent which positions a pilot drill guide tube to actively engage with the bony ridge at the penetration site and to act as the drill guide when making the pilot hole.

7. The bone engaging dental implant surgical stent placement procedure of claim 6, wherein the impression retention end of the gingival depth impression pin is of a shape, having a flat rectangular end with small holes within the flat rectangular end, which are capable of receiving a recovery cord.

8. The bone engaging dental implant surgical stent placement procedure of claim 6, wherein the stent fabrication guide tube has a first end and a second end, wherein each end is of a shape of a bevel, the bevel has an outside diameter and an inside diameter, wherein the outside diameter tapers towards the inside diameter, the inside diameter has a sharp cutting edge, wherein when force is applied to the stent fabrication guide tube the inside diameter is capable of cutting the patient's gingival tissue and the inside diameter is capable of actively engaging with the bony ridge.

9. The bone engaging dental implant surgical stent placement procedure of claim 6, wherein the stent fabrication guide wire has two ends, with each end having a sharp point capable of penetrating an artificial gingival tissue.

10. The bone engaging dental implant surgical stent placement procedure of claim 6, wherein the pilot drill guide tube has two ends and an inside diameter; the ends have of an external bevel located at one end and an internal bevel located at the other end, the external bevel tapers towards the end of the pilot drill guide tube to form a sharp cutting edge to allow the pilot drill guide tube to actively engage with the bony ridge, the internal bevel is a reversed bevel, which allows the pilot drill guide tube to act as the drill guide when making the pilot hole; the inside diameter is a few thousands of an inch larger than the drill bit, so as to allow to allow the drill bit to freely turn.

11. A bone engaging dental implant surgical stent placement method for providing a drill guide when making a pilot hole for an implant procedure, the method comprising:

penetrating a gingival bony ridge with a gingival depth impression pin to mark a penetration site;

forming an impression of the gingival depth impression pin and the gingival bony ridge with an impression material, the impression configured to record the penetration of the gingival depth impression pin;

removing the impression from the patient's mouth, and passing a stent fabrication guide tube over a penetrating end of the gingival depth impression pin, wherein the gingival depth impression pin forms an anchor for the stent fabrication guide tube;

forming a working model of the bony ridge by pouring a dental stone into the impression;

passing a stent fabrication guide pin through the stent fabrication guide tube at a penetration hole on the working model;

molding a baseplate matrix around the stent fabrication guide pin to form a constricted area in the baseplate matrix, wherein the restricted area is configured to be operable as a stent;

disengaging the stent fabrication guide pin from the stent fabrication guide tube;

manipulating a pilot drill guide tube against a gingival tissue from the gingival bony ridge to form a bleeding spot, wherein a sample of the gingival tissue is obtained from the bleeding spot;

passing the pilot drill guide tube through the hole in the stent baseplate matrix until the gingival bony ridge is engaged, wherein the pilot drill guide tube is substantially locked into position;

passing a pilot bone drill bit through the pilot drill guide tube; and directionally drilling in the penetration hole with the pilot bone drill bit.

12. The method of claim 11, wherein a round bur drill bit prepares the surface of the gingival bony ridge for reception of the pilot drill guide tube.

13. The method of claim 12, wherein the gingival tissue is obtained with a diamond bur, a tissue punch drill, or a tissue forcep.

14. The method of claim 13, wherein the baseplate matrix is molded with a dental instrument.

15. A bone engaging dental implant surgical stent placement method for providing a drill guide when making a pilot hole for an implant procedure, the method comprising:

penetrating a gingival bony ridge with a gingival depth impression pin to mark a penetration site;

forming an impression of the gingival depth impression pin and the gingival bony ridge with an impression material, the impression configured to record the penetration of the gingival depth impression pin;

removing the impression from the patient's mouth, and passing a stent fabrication guide tube over a penetrating end of the gingival depth impression pin, wherein the gingival depth impression pin forms an anchor for the stent fabrication guide tube;

forming a working model of the gingival bony ridge by pouring a dental stone into the impression;

passing a stent fabrication guide pin through the stent fabrication guide tube at a penetration hole;

molding a baseplate matrix around the stent fabrication guide pin to form a plurality of constricted areas in the baseplate matrix, wherein the plurality of restricted areas are configured to be operable as a plurality of stents;

disengaging the stent fabrication guide pin from the stent fabrication guide tube;

manipulating a plurality of pilot drill guide tubes against a gingival tissue from the gingival bony ridge to form a plurality of bleeding spots, wherein at least one sample of the gingival tissue is obtained from the plurality of bleeding spots;

passing the plurality of pilot drill guide tubes through the plurality of stents until the gingival bony ridge is engaged, wherein the plurality of pilot drill guide tubes and the baseplate matrix are substantially locked into position;

passing a plurality of pilot bone drill bits through the plurality of pilot drill guide tubes; and directionally drilling in the penetration hole with the at least one of the pilot bone drill bits, wherein the plurality of pilot drill guide tubes are configured to guide the pilot bone drill bit.

16. A bone engaging dental implant surgical stent placement method for providing a drill guide when making a pilot hole for an implant procedure, the method comprising:

penetrating a gingival bony ridge with a gingival depth impression pin to mark a penetration site;

forming an impression of the gingival depth impression pin and the gingival bony ridge with an impression material, the impression configured to record the penetration of the gingival depth impression pin;

removing the impression to reveal a penetration end from the gingival depth impression pin;

determining a depth of a gingival tissue in the gingival bony ridge by measuring the artificial gingival tissue in the impression;

setting the artificial gingival tissue with ultraviolet light;

passing a stent fabrication guide tube over the gingival depth impression pin, wherein the gingival depth impression pin forms an anchor for the stent fabrication guide tube;

forming a working model of the gingival bony ridge by pouring a dental stone into the impression;

drilling the working model with a round bur drill bit for forming a location of a penetration hole;

separating the working model from the impression;

passing a pilot bone drill bit through the penetration hole to form a pilot hole;

placing a stent fabrication guide wire into the pilot hole;

overlaying the stent fabrication guide wire with the artificial gingival tissue;

pressing the artificial gingival tissue on the stent fabrication guide wire for forming a gingival hole in the artificial gingival tissue;

replacing the stent fabrication guide wire with a long a stent fabrication guide wire;

comparing the stent fabrication guide wire with the long stent fabrication guide wire to determine if the stent fabrication guide wire is substantially parallel with the long stent fabrication guide wire;

bending the stent fabrication guide wire and/or the long stent fabrication guide wire until at least a portion of the guide wires are substantially parallel;

placing a pilot drill guide tube over the stent fabrication guide wire;

molding a baseplate matrix around the pilot drill guide tube to form a constricted area in the baseplate matrix, wherein the restricted area is configured to be operable as a stent;

placing the stent in the penetration hole;

passing the stent fabrication guide tube through the stent, wherein the stent fabrication guide tube against a gingival tissue to form a bleeding spot, wherein a sample of the gingival tissue is obtained from the bleeding spot; and passing a pilot drill guide tube through the stent until the gingival bony ridge is engaged, wherein the pilot drill guide tube is disposed to move along the length of the penetration hole and the stent for engaging the gingival bony ridge.

* * * * *